US008080254B2

(12) United States Patent
Mann et al.

(10) Patent No.: US 8,080,254 B2
(45) Date of Patent: *Dec. 20, 2011

(54) OB FUSION PROTEIN COMPOSITIONS AND METHODS

(75) Inventors: Michael B. Mann, Thousand Oaks, CA (US); Randy Ira Hecht, Thousand Oaks, CA (US); Mary Ann Pellymounter, San Diego, CA (US); Christopher Francis Toombs, Camarillo, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/525,280

(22) Filed: Sep. 22, 2006

(65) Prior Publication Data

US 2007/0020284 A1 Jan. 25, 2007

Related U.S. Application Data

(63) Continuation of application No. 11/054,085, filed on Feb. 8, 2005, now Pat. No. 7,112,659, which is a continuation of application No. 10/679,999, filed on Oct. 6, 2003, now Pat. No. 6,936,439, which is a continuation of application No. 09/568,528, filed on May 9, 2000, now abandoned, which is a continuation of application No. 09/267,517, filed on Mar. 12, 1999, now abandoned, which is a continuation of application No. 08/770,973, filed on Dec. 20, 1996, now abandoned, said application No. 09/568,528 is a continuation-in-part of application No. 09/094,931, filed on Jun. 15, 1998, now abandoned, which is a continuation of application No. 09/056,719, filed on Apr. 7, 1998, now abandoned, which is a continuation of application No. 08/561,732, filed on Nov. 22, 1995, now abandoned.

(51) Int. Cl.
*C07K 16/46* (2006.01)
*C07K 14/575* (2006.01)
*C07K 14/765* (2006.01)
*C07K 17/08* (2006.01)
*A61K 38/32* (2006.01)
*A61K 39/385* (2006.01)
*A61K 31/375* (2006.01)

(52) U.S. Cl. ............... 424/192.1; 424/193.1; 424/194.1; 424/185.1; 514/3.2; 514/5.8; 514/57; 514/59; 530/350; 530/389.1; 530/399

(58) Field of Classification Search .................... None
See application file for complete search history.

(56) References Cited

U.S. PATENT DOCUMENTS

| | | |
|---|---|---|
| 4,179,337 A | 12/1979 | Davis et al. |
| 4,925,673 A | 5/1990 | Steiner et al. |
| 5,013,556 A | 5/1991 | Woodle et al. |
| 5,073,627 A | 12/1991 | Curtis et al. |
| 5,098,833 A | 3/1992 | Lasky et al. |
| 5,116,964 A | 5/1992 | Capon et al. |
| 5,169,318 A | 12/1992 | Levy |
| 5,225,538 A | 7/1993 | Capon et al. |
| 5,284,656 A | 2/1994 | Platz et al. |
| 5,349,053 A | 9/1994 | Landolfi et al. |
| 5,428,130 A | 6/1995 | Capon et al. |
| 5,447,851 A | 9/1995 | Beutler et al. |
| 5,455,165 A | 10/1995 | Capon et al. |
| 5,480,981 A | 1/1996 | Goodwin et al. |
| 5,514,582 A | 5/1996 | Capon et al. |
| 5,594,101 A | 1/1997 | Becker et al. |
| 5,594,104 A | 1/1997 | Basinski et al. |
| 5,646,040 A | 7/1997 | Kleyn et al. |
| 5,670,625 A | 9/1997 | Baum et al. |
| 5,714,147 A | 2/1998 | Capon et al. |
| 5,739,277 A | 4/1998 | Presta et al. |
| 5,935,810 A | 8/1999 | Friedman et al. |
| 6,001,968 A | 12/1999 | Friedman et al. |
| 6,025,325 A | 2/2000 | Campfield et al. |
| 6,048,837 A | 4/2000 | Friedman et al. |
| 6,350,730 B1 | 2/2002 | Friedman et al. |
| 6,936,439 B2 | 8/2005 | Mann et al. |
| 7,112,659 B2 * | 9/2006 | Mann et al. .............. 530/350 |
| 7,208,577 B2 * | 4/2007 | Pelleymounter et al. ..... 530/350 |

FOREIGN PATENT DOCUMENTS

| | | |
|---|---|---|
| CA | 2205572 | 12/1995 |
| CA | 2195955 | 2/1996 |
| CA | 2224646 | 1/1997 |
| CA | 2238307 | 7/1997 |
| EP | 306673 | 3/1989 |
| EP | 401384 | 12/1989 |
| EP | 362999 | 4/1990 |
| EP | 417563 | 3/1991 |
| EP | 464533 | 1/1992 |
| EP | 956862 | 12/2002 |
| WO | WO 89/10932 | 11/1989 |
| WO | WO 91/11111 | 8/1991 |
| WO | WO 92/13559 | 8/1992 |

(Continued)

OTHER PUBLICATIONS

Verploregen et al, FEBS 405: 237-240, 1997.*
Mantzoro et al, Annals of Internal Medicine 130(8): 671-680, Apr. 1999.*
Abuchowski, A., et al., "Soluble Polymer-Enzyme Adducts," Enzymes as Drugs, 1981, 367-383.
Adjei, et al., "Bioavailability of Leuprolide Following Intratracheal Administration to Beagle Dogs," Int'l Journal of Pharmaceutics, 1990, 135-144, vol. 61.
Adjei, et al., Pulmonary Delivery of Peptide Drugs: Effect of Particle Size on Bioavailability of Leuprolide Acetate . . . Pharm. Res., 1990, 565-569, vol. 7, No. 6.

(Continued)

*Primary Examiner* — Phuong Huynh

(57) ABSTRACT

The present invention relates to Fc-OB fusion protein compositions, methods of preparation of such compositions and uses thereof. In particular, the present invention relates to a genetic or chemical fusion protein comprising the Fc immunoglobulin region, derivative or analog fused to the N-terminal portion of the OB protein, derivative or analog.

4 Claims, 14 Drawing Sheets

FOREIGN PATENT DOCUMENTS

| | | |
|---|---|---|
| WO | WO 94/06476 | 3/1994 |
| WO | WO 96/03141 | 2/1996 |
| WO | WO 96/04388 | 2/1996 |
| WO | WO 96/05309 | 2/1996 |
| WO | WO 96/18412 | 6/1996 |
| WO | WO 96/22308 | 7/1996 |
| WO | WO 96/31526 | 10/1996 |
| WO | WO 97/00319 | 1/1997 |
| WO | WO 97/18833 | 5/1997 |
| WO | WO 97/24137 | 7/1997 |
| WO | WO 97/24440 | 7/1997 |
| WO | WO 98/28427 | 7/1998 |
| WO | WO 98/46257 | 10/1998 |
| WO | WO 99/02711 | 1/1999 |
| WO | WO 99/22764 | 5/1999 |

OTHER PUBLICATIONS

Ashkenazi, et al., "Immunoadhesins: An Alternative to Human Monoclonal Antibodies," Methods, A Companion to Methods in Enzymology, 1995, 104-115, vol. 8.
Ashkenazi, et al., "Protection Against Edotoxic Shock by a Tumor Necrosis Factor Receptor Immunoadhesin," PNAS USA, 1991, 10535-10539, vol. 88.
Attwood, T., et al., "The Babel of Bioinformatics," Science, Oct. 2000, 471-473, vol. 290 (5491).
Bachmann, et al., "Recalibrated Linkage Map of *Escherichia coli* K-12," Bacteriological Reviews, 1976, 116-167, vol. 40.
Barinaga, M., "Obese Protein Slims Mice," Science, 1995, 475-476, vol. 269.
Bennett, B., et al., "Estracellular Domaln-IGG Fusion Proteins for Three Human Natruiretic Peptide Receptors," J. BioChem., 1991, 23060-23067, vol. 266, No. 34.
Braquet, et al., "Effect of Endothelin-1 on Blood Pressure and Bronchopulmonary System of the Guinea Pig," J. Cardiovascular Pharm., 1989, S143-S146, vol. 13 (Supp. 5).
Campfield, L.A., et al., "Recombinant Mouse OB Protein: Evidence for a Peripheral Signal Linking Adiposity and Central Neural Networks," Science, 1995, 54-549, vol. 269.
Capon, D., et al., "Designing CD4 Immunoadhesins for AIDS Therapy," Nature, Feb. 9, 1989, 525-531, vol. 337.
Debs, et al., "Lung-Specific Delivery of Cytokines Kinduces Sustained Pulmonary and Systemic Immunomodulation in Rats," J. of Immunology, 1988, 3482-3488, vol. 140, No. 10.
Devos, R., et al., "OB Protein Binds Specifically to the Choroid Plexus of Mice and Rats," PNAS, USA, May 1996, 5668-5673, vol. 93.
Ellison, et al., "The Nucleotide Sequence of a Human Immunoglobulin Cy1 Gene," Nucleic Acids Research, 1982, 4071-4079, vol. 10, No. 13.
Fisher, C., et al. "Treatement of Septic Shock With the Tumor Necrosis Factor Receptor:Fc Fusion Protein," N. Engl. J. Med., 1996, 1697-17022, vol. 334.
Francis, Focus on Growth Factors, 1992, 4-10, vol. 3.
Haak-Frendscho, M., et al., "Inhibition of Interferon-y by an Interferon-y Receptor Immunoadhesin," Immunology, 1993, 594-599, vol. 79.
Halaas, et al., "Weight-Reducing Effects of the Plasma Protein Encoded by the Obese Gene," Science, 1995, 543-546, vol. 269.
Harvey, et al., Remington's Pharmaceutical Sciences, 18th Ed., 1990, 948-1001, Mack Publishing Co., Easton, PA.
Harvill, E., et al., "An IgG3-IL2 Fusion Protein Activates Complement . . . ," Immunotechnology, 1995, 95-105, vol. 1.
Ho, S.N., et al., "Site-Directed Mutagenesis by Overlap Extension Using the Polymerase Chain Reaction," Gene, 1989, 51-59, vol. 77.
Hollenbaugh, et al., Current Protocols in Immunology, 1992, Supp., 10.19.1-10.19.11.
Hubbard, et al., "Anti-Neutrophil-Elastase Defenses of the Lower Respiratory Tract . . . " Annals of Internal Medicine, 1989, 206-212, vol. 111, No. 3.
Imagawa, K., et al., "Structure-Function Studies of Human Leptin," J. Biological Chem., 1998, 35245-35249, vol. 273, No. 52.
Kolaczynski, J., et al., "Acute and Chronic Effects of Insulin on Leptin Production in Humans: Studies in vivo and in vitro." Diabetes, 1996, 699-701, vol. 45, No. 5.
Leshner, et al., "A Simple Method for Carcass Analysis," Physiology and Behavior, 1972, 281-282, vol. 9.
Luoh, S-M., et al., "Cloning and Characterization of a Human Leptin Receptor Using a Biologically Active Letpin Immunoadhesin," J. Molecular Endo., 1997, 77-85, vol. 18.
MacDonald, et al., "Isolation of RNA Using Guranidinium Salts," Methods in Enzymology, 1987, 219-227, vol. 152.
Malik, F., et al., "Polyethylen Glycol (PEG)-modified Granulocyte-Macrophage Colony-stimulating Factor (GM-CSF) . . . ," Exp. Hematol. 1992, 1028-1035.
Mark, M., et al., "Expression and Characterization of Hepatocyte Growth Factor Receptor-IgG Fusion Proteins," J. Bio. Chem., 1992, 26166-26171, vol. 267, No. 36.
Marshall, Modem Pharmaceutics, 1979, 359-427, Marcel Dekker, Inc., NY.
Mikayama, T., et al., "Molecular Cloning and Functional Expression of a cDNA Encoding Glycosylation-Inhibiting Factor," PNAS, USA, 10056-10060, vol. 90.
Murakami, T., et al., "Cloning of a Rat Obese cDNA and Its Expression in Obese Rats," Biochem. Biophys. Res. Comm., 1995, 944-952, vol. 209, No. 3.
Newmark, et al., "Preparation and Properties of Adducts of Streptokinase and Streptokinase-Plasmin Complex . . . " J. Appl. Biochem., 1982, 185-189. vol. 4.
Ngo, et al., The Protein Folding Problem and Tertiary Structure Prediction, 491-495.
Oeswein, et al., "Aerosolization of Proteins," Proceddings of Symposium on Respiratory Dtrug Delivery II, Mar. 1990, Keystone, CO.
Pelleymounter, M.A., et al., "Effects of the Obese Gene Product on Body Weight Regulation in ob/ob Mice," Science, 1995, 540-543, vol. 269.
Prescott, et al., Microbiology, 1990, 599-602, Wm. C. Brown Publ., Dubuque, IA.
Remington's Pharmaceutical Sciences, 18th Ed., 1990, 1435-1712, Mack Publishing Co., Easton, PA.
Remington's Pharmaceutical Sciences, 18th Ed., 1990, Chapter 89, Mack Publishing Co., Easton, PA.
Sambrook, et al., Molecular Clong: A Laboratory Manual, 2nd Edition, Cold Spring Harbor Laboratory Press, Cold Spring Harbor, NY.
Skolnick, J., et all, "From Genes to Protein Structure and Function: Novel Applications of Computational Approaches . . . ," Trends in Biotech. 2000, 34-39, vol. 18.
Shin, et al., "Hybrid Antibodies," Intern. Rev. Immunol., 1993, 177-186, vol. 10.
Smith, et al., "Pulmonary Deposition and Clearance of Aerosolized Alpha-1-Proteinase Inhibitor Administered to Dogs and to Sheep," J. Clin. Invest., 1989, 1145-1154, vol. 84.
Stephens, T., et al., "The Role of Neuropeptide Y in the Antiobesity Action of the Obese Gene Product," Nature, 1995, 530-532, vol. 377.
Stryer, L., et al., Biochemistry, Third Edition, 1998, 31-33, W.H. Freeman Company, New York.
Sussman, et al., "Genetique Physiologique," C.R. Acad. Sci., 1962, 1517-1519, vol. 254, No. 8.
Van Zee, K., et al., "Protection Against Lethal *Escherichia coli* Bacteremia in Baboons (*Papio anubis*) by Pretreatment . . . ," J. of Immunology, 1996, 2221-2230, vol. 156.
Verma, I., et al., "Gene Therapy—Promises, Problems, and Prospects," Nature, 1997, 239-242, vol. 389.
Voet, D., et al., Biochemistry, 1990, 126-234, John Wiley and Sons, New York.
Zhang, et al., "Positional Cloning of the Mouse Obese Gene and its Human Homologue," Correction at Nature, 1995, 479, vol. 374.
Zhang, et al., "Positional Cloning of the Mouse Obese Gene and its Human Homologue," Nature, 1994, 425-432, vol. 372.
Zheng, X., et al., "Administration of Noncytolytic IL-10/Fc in Murine Models of Lipopolysaccharide-Induced . . . ," The Journal of Immunology, 1995, 5590-5600, vol. 154.

Hotta, K., et al., "Regulation of obses (ob) MRNA and Plasma Leptin Levels in Rhesus Monkeys," J. of Biol. Chemistry, 1996, 25327-25331, vol. 271, No. 41.

Shin, S., et al., "Transferrin-antibody Fusion Proteins Are Effective in Brain Targeting," PNAS USA, 1995, 2820-2824, vol. 92.

Casadei, J. "Expression and Secretion of Aequorin as a Chimeric Antibody by Means of a Mammalian Expression Vector," PNAS USA, 1990, 2047-2051, vol. 87.

Aruffo, A., "CD44 is the Principal Cell Surface Receptor for Hyaluronate," Cell, 1990, 1303-1313, vol. 61.

Stamenkovic, I., "The B Lymphocyte Adhesion Molecule CD22 Interacts with Leukocyte Common Antigen . . . ," Cell, 1991, 1133-1144, vol. 66.

Grundy et al., "Metabolic and health complication of obesity", Dis. Mon, vol. 36(12), pp. 641-731 (1990) (Abstract).

Ngo, et al, "Computational Complexity, Protein Structure Prediction, and the Levinthoal Paradox," The Protein Folding Problem and Tertiary Structure Prediction (1994) K. Merz, Jr. and S. LeGrand, Editors, Birkhauser Boston pp. 491-495.

* cited by examiner

Figure 1
Recombinant murine met OB (double stranded) DNA and amino acid sequence (SEQ. ID. NOs.: 1, 2, and 3).

```
       TCTAGATTTGAGTTTTAACTTTTAGAAGGAGGAATAACATATGGTACCGATCCAGAAAGT
  9    -+---------+---------+---------+---------+---------+--------  68
       AGATCTAAACTCAAAATTGAAAATCTTCCTCCTTATTGTATACCATGGCTAGGTCTTTCA
                                              M  V  P  I  Q  K  V  -

TCAGGACGACACCAAAACCTTAATTAAAACGATCGTTACGCGTATCAACGACATCAGTCA
 69    -+---------+---------+---------+---------+---------+-------- 128
       AGTCCTGCTGTGGTTTTGGAATTAATTTTGCTAGCAATGCGCATAGTTGCTGTAGTCAGT
        Q  D  D  T  K  T  L  I  K  T  I  V  T  R  I  N  D  I  S  H  -

CACCCAGTCGGTCTCCGCTAAACAGCGTGTTACCGGTCTGGACTTCATCCCGGGTCTGCA
129    -+---------+---------+---------+---------+---------+-------- 188
       GTGGGTCAGCCAGAGGCGATTTGTCGCACAATGGCCAGACCTGAAGTAGGGCCCAGACGT
        T  Q  S  V  S  A  K  Q  R  V  T  G  L  D  F  I  P  G  L  H  -

CCCGATCCTAAGCTTGTCCAAAATGGACCAGACCCTGGCTGTATACCAGCAGGTGTTAAC
189    -+---------+---------+---------+---------+---------+-------- 248
       GGGCTAGGATTCGAACAGGTTTTACCTGGTCTGGGACCGACATATGGTCGTCCACAATTG
        P  I  L  S  L  S  K  M  D  Q  T  L  A  V  Y  Q  Q  V  L  T  -

CTCCCTGCCGTCCCAGAACGTTCTTCAGATCGCTAACGACCTCGAGAACCTTCGCGACCT
249    -+---------+---------+---------+---------+---------+-------- 308
       GAGGGACGGCAGGGTCTTGCAAGAAGTCTAGCGATTGCTGGAGCTCTTGGAAGCGCTGGA
        S  L  P  S  Q  N  V  L  Q  I  A  N  D  L  E  N  L  R  D  L  -

GCTGCACCTGCTGGCATTCTCCAAATCCTGCTCCCTGCCGCAGACCTCAGGTCTTCAGAA
309    -+---------+---------+---------+---------+---------+-------- 368
       CGACGTGGACGACCGTAAGAGGTTTAGGACGAGGGACGGCGTCTGGAGTCCAGAAGTCTT
        L  H  L  L  A  F  S  K  S  C  S  L  P  Q  T  S  G  L  Q  K  -

ACCGGAATCCCTGGACGGGGTCCTGGAAGCATCCCTGTACAGCACCGAAGTTGTTGCTCT
369    -+---------+---------+---------+---------+---------+-------- 428
       TGGCCTTAGGGACCTGCCCCAGGACCTTCGTAGGGACATGTCGTGGCTTCAACAACGAGA
        P  E  S  L  D  G  V  L  E  A  S  L  Y  S  T  E  V  V  A  L  -

GTCCCGTCTGCAGGGTTCCCTTCAGGACATCCTTCAGCAGCTGGACGTTTCTCCGGAATG
429    -+---------+---------+---------+---------+---------+-------- 488
       CAGGGCAGACGTCCCAAGGGAAGTCCTGTAGGAAGTCGTCGACCTGCAAAGAGGCCTTAC
        S  R  L  Q  G  S  L  Q  D  I  L  Q  Q  L  D  V  S  P  E  C  -

TTAATGGATCC
489    -+---------
       AATTACCTAGG
```

Figure 2

Recombinant human met OB analog (Double Stranded) DNA and amino acid sequence (SEQ. ID. NOs.: 4, 5 and 6).

```
     CATATGGTACCGATCCAGAAAGTTCAGGACGACACCAAAACCTTAATTAAAACGATCGTT
  1  ------------+---------+---------+---------+---------+---------+  60
     GTATACCATGGCTAGGTCTTTCAAGTCCTGCTGTGGTTTTGGAATTAATTTTGCTAGCAA

M  V  P  I  Q  K  V  Q  D  D  T  K  T  L  I  K  T  I  V  -

ACGCGTATCAACGACATCAGTCACACCCAGTCGGTGAGCTCTAAACAGCGTGTTACAGGC
 61  ------------+---------+---------+---------+---------+---------+ 120
     TGCGCATAGTTGCTGTAGTCAGTGTGGGTCAGCCACTCGAGATTTGTCGCACAATGTCCG

T  R  I  N  D  I  S  H  T  Q  S  V  S  S  K  Q  R  V  T  G  -

CTGGACTTCATCCCGGGTCTGCACCCGATCCTGACCTTGTCCAAAATGGACCAGACCCTG
121  ------------+---------+---------+---------+---------+---------+ 180
     GACCTGAAGTAGGGCCCAGACGTGGGCTAGGACTGGAACAGGTTTTACCTGGTCTGGGAC

L  D  F  I  P  G  L  H  P  I  L  T  L  S  K  M  D  Q  T  L  -

GCTGTATACCAGCAGATCTTAACCTCCATGCCGTCCCGTAACGTTCTTCAGATCTCTAAC
181  ------------+---------+---------+---------+---------+---------+ 240
     CGACATATGGTCGTCTAGAATTGGAGGTACGGCAGGGCATTGCAAGAAGTCTAGAGATTG

A  V  Y  Q  Q  I  L  T  S  M  P  S  R  N  V  L  Q  I  S  N  -

GACCTCGAGAACCTTCGCGACCTGCTGCACGTGCTGGCATTCTCCAAATCCTGCCACCTG
241  ------------+---------+---------+---------+---------+---------+ 300
     CTGGAGCTCTTGGAAGCGCTGGACGACGTGCACGACCGTAAGAGGTTTAGGACGGTGGAC

D  L  E  N  L  R  D  L  L  H  V  L  A  F  S  K  S  C  H  L  -

CCATGGGCTTCAGGTCTTGAGACTCTGGACTCTCTGGGCGGGGTCCTGGAAGCATCCGGT
301  ------------+---------+---------+---------+---------+---------+ 360
     GGTACCCGAAGTCCAGAACTCTGAGACCTGAGAGACCCGCCCCAGGACCTTCGTAGGCCA

P  W  A  S  G  L  E  T  L  D  S  L  G  G  V  L  E  A  S  G  -

TACAGCACCGAAGTTGTTGCTCTGTCCCGTCTGCAGGGTTCCCTTCAGGACATGCTTTGG
361  ------------+---------+---------+---------+---------+---------+ 420
     ATGTCGTGGCTTCAACAACGAGACAGGGCAGACGTCCCAAGGGAAGTCCTGTACGAAACC

Y  S  T  E  V  V  A  L  S  R  L  Q  G  S  L  Q  D  M  L  W  -

CAGCTGGACCTGTCTCCGGGTTGTTAATGGATCC
421  ------------+---------+---------+---- 454
     GTCGACCTGGACAGAGGCCCAACAATTACCTAGG

Q  L  D  L  S  P  G  C  *
```

Figure 3A
Recombinant human metFc-OB (double stranded) DNA and amino acid sequence (SEQ. ID. NOs.: 7, 8 and 9).

```
       CATATGGAACCCAAATCTTGTGACAAAACTCACACATGCCCACCGTGCCCAGCACCTGAA
  1    ------------+---------+---------+---------+---------+---------+  60
       GTATACCTTGGGTTTAGAACACTGTTTTGAGTGTGTACGGGTGGCACGGGTCGTGGACTT

M  E  P  K  S  C  D  K  T  H  T  C  P  P  C  P  A  P  E   -

CTCCTGGGGGGACCGTCAGTCTTCCTCTTCCCCCCAAAACCCAAGGACACCCTCATGATC
 61    ------------+---------+---------+---------+---------+---------+ 120
       GAGGACCCCCCTGGCAGTCAGAAGGAGAAGGGGGGTTTTGGGTTCCTGTGGGAGTACTAG

L  L  G  P  S  V  F  L  F  P  P  K  P  K  D  T  L  M  I   -

TCCCGGACCCCTGAGGTCACATGCGTGGTGGTGGACGTGAGCCACGAAGACCCTGAGGTC
121    ------------+---------+---------+---------+---------+---------+ 180
       AGGGCCTGGGGACTCCAGTGTACGCACCACCACCTGCACTCGGTGCTTCTGGGACTCCAG

S  R  T  P  E  V  T  C  V  V  V  D  V  S  H  E  D  P  E  V  -

AAGTTCAACTGGTACGTGGACGGCGTGGAGGTGCATAATGCCAAGACAAAGCCGCGGGAG
181    ------------+---------+---------+---------+---------+---------+ 240
       TTCAAGTTGACCATGCACCTGCCGCACCTCCACGTATTACGGTTCTGTTTCGGCGCCCTC

K  F  N  W  Y  V  D  G  V  E  V  H  N  A  K  T  K  P  R  E  -

GAGCAGTACAACAGCACGTACCGTGTGGTCAGCGTCCTCACCGTCCTGCACCAGGACTGG
241    ------------+---------+---------+---------+---------+---------+ 300
       CTCGTCATGTTGTCGTGCATGGCACACCAGTCGCAGGAGTGGCAGGACGTGGTCCTGACC

E  Q  Y  N  S  T  Y  R  V  V  S  V  L  T  V  L  H  Q  D  W  -

CTGAATGGCAAGGAGTACAAGTGCAAGGTCTCCAACAAAGCCCTCCCAGCCCCCATCGAG
301    ------------+---------+---------+---------+---------+---------+ 360
       GACTTACCGTTCCTCATGTTCACGTTCCAGAGGTTGTTTCGGGAGGGTCGGGGGTAGCTC

L  N  G  K  E  Y  K  C  K  V  S  N  K  A  L  P  A  P  I  E  -

AAAACCATCTCCAAAGCCAAAGGGCAGCCCCGAGAACCACAGGTGTACACCCTGCCCCCA
361    ------------+---------+---------+---------+---------+---------+ 420
       TTTTGGTAGAGGTTTCGGTTTCCCGTCGGGGCTCTTGGTGTCCACATGTGGGACGGGGT

K  T  I  S  K  A  K  G  Q  P  R  E  P  Q  V  Y  T  L  P  P  -

TCCCGGGATGAGCTGACCAAGAACCAGGTCAGCCTGACCTGCCTGGTCAAAGGCTTCTAT
421    ------------+---------+---------+---------+---------+---------+ 480
       AGGGCCCTACTCGACTGGTTCTTGGTCCAGTCGGACTGGACGGACCAGTTTCCGAAGATA

S  R  D  E  L  T  K  N  Q  V  S  L  T  C  L  V  K  G  F  Y  -

CCCAGCGACATCGCCGTGGAGTGGGAGAGCAATGGGCAGCCGGAGAACAACTACAAGACC
481    ------------+---------+---------+---------+---------+---------+ 540
       GGGTCGCTGTAGCGGCACCTCACCCTCTCGTTACCCGTCGGCCTCTTGTTGATGTTCTGG
```

Figure 3B

```
            P  S  D  I  A  V  E  W  E  S  N  G  Q  P  E  N  N  Y  K  T   -
       ACGCCTCCCGTGCTGGACTCCGACGGCTCCTTCTTCCTCTACAGCAAGCTCACCGTGGAC
541    --------+---------+---------+---------+---------+---------+  600
       TGCGGAGGGCACGACCTGAGGCTGCCGAGGAAGAAGGAGATGTCGTTCGAGTGGCACCTG

T  P  P  V  L  D  S  D  G  S  F  F  L  Y  S  K  L  T  V  D   -
       AAGAGCAGGTGGCAGCAGGGGAACGTCTTCTCATGCTCCGTGATGCATGAGGCTCTGCAC
601    --------+---------+---------+---------+---------+---------+  660
       TTCTCGTCCACCGTCGTCCCCTTGCAGAAGAGTACGAGGCACTACGTACTCCGAGACGTG

K  S  R  W  Q  Q  G  N  V  F  S  C  S  V  M  H  E  A  L  H   -
       AACCACTACACGCAGAAGAGCCTCTCCCTGTCTCCGGGTAAAGTACCGATCCAGAAAGTT
661    --------+---------+---------+---------+---------+---------+  720
       TTGGTGATGTGCGTCTTCTCGGAGAGGGACAGAGGCCCATTTCATGGCTAGGTCTTTCAA

N  H  Y  T  Q  K  S  L  S  L  S  P  G  K  V  P  I  Q  K  V   -
       CAGGACGACACCAAAACCTTAATTAAAACGATCGTTACGCGTATCAACGACATCAGTCAC
721    --------+---------+---------+---------+---------+---------+  780
       GTCCTGCTGTGGTTTTGGAATTAATTTTGCTAGCAATGCGCATAGTTGCTGTAGTCAGTG

Q  D  D  T  K  T  L  I  K  T  I  V  T  R  I  N  D  I  S  H   -
       ACCCAGTCGGTGAGCTCTAAACAGAAAGTTACAGGCCTGGACTTCATCCCGGGTCTGCAC
781    --------+---------+---------+---------+---------+---------+  840
       TGGGTCAGCCACTCGAGATTTGTCTTTCAATGTCCGGACCTGAAGTAGGGCCCAGACGTG

T  Q  S  V  S  S  K  Q  K  V  T  G  L  D  F  I  P  G  L  H   -
       CCGATCCTGACCTTGTCCAAAATGGACCAGACCCTGGCTGTATACCAGCAGATCTTAACC
841    --------+---------+---------+---------+---------+---------+  900
       GGCTAGGACTGGAACAGGTTTTACCTGGTCTGGGACCGACATATGGTCGTCTAGAATTGG

P  I  L  T  L  S  K  M  D  Q  T  L  A  V  Y  Q  Q  I  L  T   -
       TCCATGCCGTCCCGTAACGTTATCCAGATCTCTAACGACCTCGAGAACCTTCGCGACCTG
901    --------+---------+---------+---------+---------+---------+  960
       AGGTACGGCAGGGCATTGCAATAGGTCTAGAGATTGCTGGAGCTCTTGGAAGCGCTGGAC

S  M  P  S  R  N  V  I  Q  I  S  N  D  L  E  N  L  R  D  L   -
       CTGCACGTGCTGGCATTCTCCAAATCCTGCCACCTGCCATGGGCTTCAGGTCTTGAGACT
961    --------+---------+---------+---------+---------+---------+  1020
       GACGTGCACGACCGTAAGAGGTTTAGGACGGTGGACGGTACCCGAAGTCCAGAACTCTGA

L  H  V  L  A  F  S  K  S  C  H  L  P  W  A  S  G  L  E  T   -
       CTGGACTCTCTGGGCGGGGTCCTGGAAGCATCCGGTTACAGCACCGAAGTTGTTGCTCTG
1021   --------+---------+---------+---------+---------+---------+  1080
       GACCTGAGAGACCCGCCCCAGGACCTTCGTAGGCCAATGTCGTGGCTTCAACAACGAGAC

```
        TCCCGTCTGCAGGGTTCCCTTCAGGACATGCTTTGGCAGCTGGACCTGTCTCCGGGTTGT
1081    ---------+---------+---------+---------+---------+---------+ 1140
        AGGGCAGACGTCCCAAGGGAAGTCCTGTACGAAACCGTCGACCTGGACAGAGGCCCAACA

S   R   L   Q   G   S   L   Q   D   M   L   W   Q   L   D   L   S   P   G   C   -

TAATGGATCC
1141    ---------+ 1150
        ATTACCTAGG
```

Figure 4A

Recombinant human metFc-OB (double stranded) DNA and amino acid sequence (SEQ. ID. NOs.: 10, 11 and 12).

```
    CATATGGAACCAAAATCTGCTGACAAAACTCACACATGTCCACCTTGTCCAGCTCCGGAA
1   ---------+---------+---------+---------+---------+---------+  60
    GTATACCTTGGTTTTAGACGACTGTTTTGAGTGTGTACAGGTGGAACAGGTCGAGGCCTT

M  E  P  K  S  A  D  K  T  H  T  C  P  P  C  P  A  P  E    -

CTCCTGGGGGGTCCTTCAGTCTTCCTCTTCCCCCCAAAACCCAAGGACACCCTCATGATC
61  ---------+---------+---------+---------+---------+---------+ 120
    GAGGACCCCCCAGGAAGTCAGAAGGAGAAGGGGGGTTTTGGGTTCCTGTGGGAGTACTAG

L  L  G  G  P  S  V  F  L  F  P  P  K  P  K  D  T  L  M  I -

TCCCGGACCCCTGAGGTCACATGCGTGGTGGTGGACGTGAGCCACGAAGACCCTGAGGTC
121 ---------+---------+---------+---------+---------+---------+ 180
    AGGGCCTGGGGACTCCAGTGTACGCACCACCACCTGCACTCGGTGCTTCTGGGACTCCAG

S  R  T  P  E  V  T  C  V  V  V  D  V  S  H  E  D  P  E  V -

AAGTTCAACTGGTACGTGGACGGCGTGGAGGTGCATAATGCCAAGACAAAGCCGCGGGAG
181 ---------+---------+---------+---------+---------+---------+ 240
    TTCAAGTTGACCATGCACCTGCCGCACCTCCACGTATTACGGTTCTGTTTCGGCGCCCTC

K  F  N  W  Y  V  D  G  V  E  V  H  N  A  K  T  K  P  R  E -

GAGCAGTACAACAGCACGTACCGTGTGGTCAGCGTCCTCACCGTCCTGCACCAGGACTGG
241 ---------+---------+---------+---------+---------+---------+ 300
    CTCGTCATGTTGTCGTGCATGGCACACCAGTCGCAGGAGTGGCAGGACGTGGTCCTGACC

E  Q  Y  N  S  T  Y  R  V  V  S  V  L  T  V  L  H  Q  D  W -

CTGAATGGCAAGGAGTACAAGTGCAAGGTCTCCAACAAAGCCCTCCCAGCCCCCATCGAG
301 ---------+---------+---------+---------+---------+---------+ 360
    GACTTACCGTTCCTCATGTTCACGTTCCAGAGGTTGTTTCGGGAGGGTCGGGGGTAGCTC

L  N  G  K  E  Y  K  C  K  V  S  N  K  A  L  P  A  P  I  E -

AAAACCATCTCCAAAGCCAAAGGGCAGCCCCGAGAACCACAGGTGTACACCCTGCCCCCA
361 ---------+---------+---------+---------+---------+---------+ 420
    TTTTGGTAGAGGTTTCGGTTTCCCGTCGGGGCTCTTGGTGTCCACATGTGGGACGGGGGT

K  T  I  S  K  A  K  G  Q  P  R  E  P  Q  V  Y  T  L  P  P -

TCCCGGGATGAGCTGACCAAGAACCAGGTCAGCCTGACCTGCCTGGTCAAAGGCTTCTAT
421 ---------+---------+---------+---------+---------+---------+ 480
    AGGGCCCTACTCGACTGGTTCTTGGTCCAGTCGGACTGGACGGACCAGTTTCCGAAGATA

S  R  D  E  L  T  K  N  Q  V  S  L  T  C  L  V  K  G  F  Y -

CCCAGCGACATCGCCGTGGAGTGGGAGAGCAATGGGCAGCCGGAGAACAACTACAAGACC
481 ---------+---------+---------+---------+---------+---------+ 540
    GGGTCGCTGTAGCGGCACCTCACCCTCTCGTTACCCGTCGGCCTCTTGTTGATGTTCTGG
```

Figure 4B

```
              P   S   D   I   A   V   E   W   E   S   N   G   Q   P   E   N   N   Y   K   T  -
       ACGCCTCCCGTGCTGGACTCCGACGGCTCCTTCTTCCTCTACAGCAAGCTCACCGTGGAC
541    ---------+---------+---------+---------+---------+---------+  600
       TGCGGAGGGCACGACCTGAGGCTGCCGAGGAAGAAGGAGATGTCGTTCGAGTGGCACCTG

T   P   P   V   L   D   S   D   G   S   F   F   L   Y   S   K   L   T   V   D  -
       AAGAGCAGGTGGCAGCAGGGGAACGTCTTCTCATGCTCCGTGATGCATGAGGCTCTGCAC
601    ---------+---------+---------+---------+---------+---------+  660
       TTCTCGTCCACCGTCGTCCCCTTGCAGAAGAGTACGAGGCACTACGTACTCCGAGACGTG

K   S   R   W   Q   Q   G   N   V   F   S   C   S   V   M   H   E   A   L   H  -
       AACCACTACACGCAGAAGAGCCTCTCCCTGTCTCCGGGTAAAGTACCGATCCAGAAAGTT
661    ---------+---------+---------+---------+---------+---------+  720
       TTGGTGATGTGCGTCTTCTCGGAGAGGGACAGAGGCCCATTTCATGGCTAGGTCTTTCAA

N   H   Y   T   Q   K   S   L   S   L   S   P   G   K   V   P   I   Q   K   V  -
       CAGGACGACACCAAAACCTTAATTAAAACGATCGTTACGCGTATCAACGACATCAGTCAC
721    ---------+---------+---------+---------+---------+---------+  780
       GTCCTGCTGTGGTTTTGGAATTAATTTTGCTAGCAATGCGCATAGTTGCTGTAGTCAGTG

Q   D   D   T   K   T   L   I   K   T   I   V   T   R   I   N   D   I   S   H  -
       ACCCAGTCGGTGAGCTCTAAACAGAAAGTTACAGGCCTGGACTTCATCCCGGGTCTGCAC
781    ---------+---------+---------+---------+---------+---------+  840
       TGGGTCAGCCACTCGAGATTTGTCTTTCAATGTCCGGACCTGAAGTAGGGCCCAGACGTG

T   Q   S   V   S   S   K   Q   K   V   T   G   L   D   F   I   P   G   L   H  -
       CCGATCCTGACCTTGTCCAAAATGGACCAGACCCTGGCTGTATACCAGCAGATCTTAACC
841    ---------+---------+---------+---------+---------+---------+  900
       GGCTAGGACTGGAACAGGTTTTACCTGGTCTGGGACCGACATATGGTCGTCTAGAATTGG

P   I   L   T   L   S   K   M   D   Q   T   L   A   V   Y   Q   Q   I   L   T  -
       TCCATGCCGTCCCGTAACGTTATCCAGATCTCTAACGACCTCGAGAACCTTCGCGACCTG
901    ---------+---------+---------+---------+---------+---------+  960
       AGGTACGGCAGGGCATTGCAATAGGTCTAGAGATTGCTGGAGCTCTTGGAAGCGCTGGAC

S   M   P   S   R   N   V   I   Q   I   S   N   D   L   E   N   L   R   D   L  -
       CTGCACGTGCTGGCATTCTCCAAATCCTGCCACCTGCCATGGGCTTCAGGTCTTGAGACT
961    ---------+---------+---------+---------+---------+---------+  1020
       GACGTGCACGACCGTAAGAGGTTTAGGACGGTGGACGGTACCCGAAGTCCAGAACTCTGA

L   H   V   L   A   F   S   K   S   C   H   L   P   W   A   S   G   L   E   T  -
       CTGGACTCTCTGGGCGGGGTCCTGGAAGCATCCGGTTACAGCACCGAAGTTGTTGCTCTG
1021   ---------+---------+---------+---------+---------+---------+. 1080
       GACCTGAGAGACCCGCCCCAGGACCTTCGTAGGCCAATGTCGTGGCTTCAACAACGAGAC

```
       TCCCGTCTGCAGGGTTCCCTTCAGGACATGCTTTGGCAGCTGGACCTGTCTCCGGGTTGT
1081   ---------+---------+---------+---------+---------+---------+ 1140
       AGGGCAGACGTCCCAAGGGAAGTCCTGTACGAAACCGTCGACCTGGACAGAGGCCCAACA

S   R   L   Q   G   S   L   Q   D   M   L   W   Q   L   D   L   S   P   G   C   -

TAATGGATCC
1141   ---------+ 1150
       ATTACCTAGG
```

Figure 5A

Recombinant human metFc-OB (double stranded) DNA and amino acid sequence (SEQ. ID. NOs.: 13, 14 and 15).

```
    CATATGGACAAAACTCACACATGTCCACCTTGTCCAGCTCCGGAACTCCTGGGGGGTCCT
  1 ---------+---------+---------+---------+---------+---------+ 60
    GTATACCTGTTTTGAGTGTGTACAGGTGGAACAGGTCGAGGCCTTGAGGACCCCCCAGGA

M  D  K  T  H  T  C  P  P  C  P  A  P  E  L  L  G  G  P  -

TCAGTCTTCCTCTTCCCCCCAAAACCCAAGGACACCCTCATGATCTCCCGGACCCCTGAG
 61 ---------+---------+---------+---------+---------+---------+ 120
    AGTCAGAAGGAGAAGGGGGGTTTTGGGTTCCTGTGGGAGTACTAGAGGGCCTGGGGACTC

S  V  F  L  F  P  P  K  P  K  D  T  L  M  I  S  R  T  P  E  -

GTCACATGCGTGGTGGTGGACGTGAGCCACGAAGACCCTGAGGTCAAGTTCAACTGGTAC
121 ---------+---------+---------+---------+---------+---------+ 180
    CAGTGTACGCACCACCACCTGCACTCGGTGCTTCTGGGACTCCAGTTCAAGTTGACCATG

V  T  C  V  V  V  D  V  S  H  E  D  P  E  V  K  F  N  W  Y  -

GTGGACGGCGTGGAGGTGCATAATGCCAAGACAAAGCCGCGGGAGGAGCAGTACAACAGC
181 ---------+---------+---------+---------+---------+---------+ 240
    CACCTGCCGCACCTCCACGTATTACGGTTCTGTTTCGGCGCCCTCCTCGTCATGTTGTCG

V  D  G  V  E  V  H  N  A  K  T  K  P  R  E  E  Q  Y  N  S  -

ACGTACCGTGTGGTCAGCGTCCTCACCGTCCTGCACCAGGACTGGCTGAATGGCAAGGAG
241 ---------+---------+---------+---------+---------+---------+ 300
    TGCATGGCACACCAGTCGCAGGAGTGGCAGGACGTGGTCCTGACCGACTTACCGTTCCTC

T  Y  R  V  V  S  V  L  T  V  L  H  Q  D  W  L  N  G  K  E  -

TACAAGTGCAAGGTCTCCAACAAAGCCCTCCCAGCCCCCATCGAGAAAACCATCTCCAAA
301 ---------+---------+---------+---------+---------+---------+ 360
    ATGTTCACGTTCCAGAGGTTGTTTCGGGAGGGTCGGGGGTAGCTCTTTTGGTAGAGGTTT

Y  K  C  K  V  S  N  K  A  L  P  A  P  I  E  K  T  I  S  K  -

GCCAAAGGGCAGCCCCGAGAACCACAGGTGTACACCCTGCCCCCATCCCGGGATGAGCTG
361 ---------+---------+---------+---------+---------+---------+ 420
    CGGTTTCCCGTCGGGGCTCTTGGTGTCCACATGTGGGACGGGGGTAGGGCCCTACTCGAC

A  K  G  Q  P  R  E  P  Q  V  Y  T  L  P  P  S  R  D  E  L  -

ACCAAGAACCAGGTCAGCCTGACCTGCCTGGTCAAAGGCTTCTATCCCAGCGACATCGCC
421 ---------+---------+---------+---------+---------+---------+ 480
    TGGTTCTTGGTCCAGTCGGACTGGACGGACCAGTTTCCGAAGATAGGGTCGCTGTAGCGG

T  K  N  Q  V  S  L  T  C  L  V  K  G  F  Y  P  S  D  I  A  -

GTGGAGTGGGAGAGCAATGGGCAGCCGGAGAACAACTACAAGACCACGCCTCCCGTGCTG
481 ---------+---------+---------+---------+---------+---------+ 540
    CACCTCACCCTCTCGTTACCCGTCGGCCTCTTGTTGATGTTCTGGTGCGGAGGGCACGAC
```

Figure 5B

```
          V  E  W  E  S  N  G  Q  P  E  N  N  Y  K  T  T  P  P  V  L   -
      GACTCCGACGGCTCCTTCTTCCTCTACAGCAAGCTCACCGTGGACAAGAGCAGGTGGCAG
541   ---------+---------+---------+---------+---------+---------+ 600
      CTGAGGCTGCCGAGGAAGAAGGAGATGTCGTTCGAGTGGCACCTGTTCTCGTCCACCGTC

D  S  D  G  S  F  F  L  Y  S  K  L  T  V  D  K  S  R  W  Q   -
      CAGGGGAACGTCTTCTCATGCTCCGTGATGCATGAGGCTCTGCACAACCACTACACGCAG
601   ---------+---------+---------+---------+---------+---------+ 660
      GTCCCCTTGCAGAAGAGTACGAGGCACTACGTACTCCGAGACGTGTTGGTGATGTGCGTC

Q  G  N  V  F  S  C  S  V  M  H  E  A  L  H  N  H  Y  T  Q   -
      AAGAGCCTCTCCCTGTCTCCGGGTAAAGTACCGATCCAGAAAGTTCAGGACGACACCAAA
661   ---------+---------+---------+---------+---------+---------+ 720
      TTCTCGGAGAGGGACAGAGGCCCATTTCATGGCTAGGTCTTTCAAGTCCTGCTGTGGTTT

K  S  L  S  L  S  P  G  K  V  P  I  Q  K  V  Q  D  D  T  K   -
      ACCTTAATTAAAACGATCGTTACGCGTATCAACGACATCAGTCACACCCAGTCGGTGAGC
721   ---------+---------+---------+---------+---------+---------+ 780
      TGGAATTAATTTTGCTAGCAATGCGCATAGTTGCTGTAGTCAGTGTGGGTCAGCCACTCG

T  L  I  K  T  I  V  T  R  I  N  D  I  S  H  T  Q  S  V  S   -
      TCTAAACAGAAAGTTACAGGCCTGGACTTCATCCCGGGTCTGCACCCGATCCTGACCTTG
781   ---------+---------+---------+---------+---------+---------+ 840
      AGATTTGTCTTTCAATGTCCGGACCTGAAGTAGGGCCCAGACGTGGGCTAGGACTGGAAC

S  K  Q  K  V  T  G  L  D  F  I  P  G  L  H  P  I  L  T  L   -
      TCCAAAATGGACCAGACCCTGGCTGTATACCAGCAGATCTTAACCTCCATGCCGTCCCGT
841   ---------+---------+---------+---------+---------+---------+ 900
      AGGTTTTACCTGGTCTGGGACCGACATATGGTCGTCTAGAATTGGAGGTACGGCAGGGCA

S  K  M  D  Q  T  L  A  V  Y  Q  Q  I  L  T  S  M  P  S  R   -
      AACGTTATCCAGATCTCTAACGACCTCGAGAACCTTCGCGACCTGCTGCACGTGCTGGCA
901   ---------+---------+---------+---------+---------+---------+ 960
      TTGCAATAGGTCTAGAGATTGCTGGAGCTCTTGGAAGCGCTGGACGACGTGCACGACCGT

N  V  I  Q  I  S  N  D  L  E  N  L  R  D  L  L  H  V  L  A   -
      TTCTCCAAATCCTGCCACCTGCCATGGGCTTCAGGTCTTGAGACTCTGGACTCTCTGGGC
961   ---------+---------+---------+---------+---------+---------+ 1020
      AAGAGGTTTAGGACGGTGGACGGTACCCGAAGTCCAGAACTCTGAGACCTGAGAGACCCG

F  S  K  S  C  H  L  P  W  A  S  G  L  E  T  L  D  S  L  G   -
      GGGGTCCTGGAAGCATCCGGTTACAGCACCGAAGTTGTTGCTCTGTCCCGTCTGCAGGGT
1021  ---------+---------+---------+---------+---------+---------+ 1080
      CCCCAGGACCTTCGTAGGCCAATGTCGTGGCTTCAACAACGAGACAGGGCAGACGTCCCA

```
      TCCCTTCAGGACATGCTTTGGCAGCTGGACCTGTCTCCGGGTTGTTAATGGATCC
1081  ---------+---------+---------+---------+---------+-----  1135
      AGGGAAGTCCTGTACGAAACCGTCGACCTGGACAGAGGCCCAACAATTACCTAGG

Recombinant human metFc-OB (double stranded) DNA and amino acid sequence (SEQ. ID. NOs.: 16, 17 and 18).

```
     CATATGGACAAAACTCACACATGCCCACCGTGCCCAGCTCCGGAACTCGAAGGTGGTCCG
  1  ---------+---------+---------+---------+---------+---------+ 60
     GTATACCTGTTTTGAGTGTGTACGGGTGGCACGGGTCGAGGCCTTGAGCTTCCACCAGGC

M   D   K   T   H   T   C   P   P   C   P   A   P   E   L   E   G   G   P   -

TCAGTCTTCCTCTTCCCCCCAAAACCCAAGGACACCCTCATGATCTCCCGGACCCCTGAG
 61  ---------+---------+---------+---------+---------+---------+ 120
     AGTCAGAAGGAGAAGGGGGGTTTTGGGTTCCTGTGGGAGTACTAGAGGGCCTGGGGACTC

S   V   F   L   F   P   P   K   P   K   D   T   L   M   I   S   R   T   P   E   -

GTCACATGCGTGGTGGTGGACGTGAGCCACGAAGACCCTGAGGTCAAGTTCAACTGGTAC
 121 ---------+---------+---------+---------+---------+---------+ 180
     CAGTGTACGCACCACCACCTGCACTCGGTGCTTCTGGGACTCCAGTTCAAGTTGACCATG

V   T   C   V   V   V   D   V   S   H   E   D   P   E   V   K   F   N   W   Y   -

GTGGACGGCGTGGAGGTGCATAATGCCAAGACAAAGCCGCGGGAGGAGCAGTACAACAGC
 181 ---------+---------+---------+---------+---------+---------+ 240
     CACCTGCCGCACCTCCACGTATTACGGTTCTGTTTCGGCGCCCTCCTCGTCATGTTGTCG

V   D   G   V   E   V   H   N   A   K   T   K   P   R   E   E   Q   Y   N   S   -

ACGTACCGTGTGGTCAGCGTCCTCACCGTCCTGCACCAGGACTGGCTGAATGGCAAAGCT
 241 ---------+---------+---------+---------+---------+---------+ 300
     TGCATGGCACACCAGTCGCAGGAGTGGCAGGACGTGGTCCTGACCGACTTACCGTTTCGA

T   Y   R   V   V   S   V   L   T   V   L   H   Q   D   W   L   N   G   K   A   -

TACGCATGCGCGGTCTCCAACAAAGCCCTCCCAGCCCCCATCGAGAAAACCATCTCCAAA
 301 ---------+---------+---------+---------+---------+---------+ 360
     ATGCGTACGCGCCAGAGGTTGTTTCGGGAGGGTCGGGGGTAGCTCTTTTGGTAGAGGTTT

Y   A   C   A   V   S   N   K   A   L   P   A   P   I   E   K   T   I   S   K   -

GCCAAAGGGCAGCCCCGAGAACCACAGGTGTACACCCTGCCCCCATCCCGGGATGAGCTG
 361 ---------+---------+---------+---------+---------+---------+ 420
     CGGTTTCCCGTCGGGGCTCTTGGTGTCCACATGTGGGACGGGGGTAGGGCCCTACTCGAC

A   K   G   Q   P   R   E   P   Q   V   Y   T   L   P   P   S   R   D   E   L   -

ACCAAGAACCAGGTCAGCCTGACCTGCCTGGTCAAAGGCTTCTATCCCAGCGACATCGCC
 421 ---------+---------+---------+---------+---------+---------+ 480
     TGGTTCTTGGTCCAGTCGGACTGGACGGACCAGTTTCCGAAGATAGGGTCGCTGTAGCGG

T   K   N   Q   V   S   L   T   C   L   V   K   G   F   Y   P   S   D   I   A   -

GTGGAGTGGGAGAGCAATGGGCAGCCGGAGAACAACTACAAGACCACGCCTCCCGTGCTG
 481 ---------+---------+---------+---------+---------+---------+ 540
     CACCTCACCCTCTCGTTACCCGTCGGCCTCTTGTTGATGTTCTGGTGCGGAGGGCACGAC
```

Figure 6B

```
         V   E   W   E   S   N   G   Q   P   E   N   N   Y   K   T   T   P   P   V   L   -
      GACTCCGACGGCTCCTTCTTCCTCTACAGCAAGCTCACCGTGGACAAGAGCAGGTGGCAG
541   ---------+---------+---------+---------+---------+---------+ 600
      CTGAGGCTGCCGAGGAAGAAGGAGATGTCGTTCGAGTGGCACCTGTTCTCGTCCACCGTC

D   S   D   G   S   F   F   L   Y   S   K   L   T   V   D   K   S   R   W   Q   -
      CAGGGGAACGTCTTCTCATGCTCCGTGATGCATGAGGCTCTGCACAACCACTACACGCAG
601   ---------+---------+---------+---------+---------+---------+ 660
      GTCCCCTTGCAGAAGAGTACGAGGCACTACGTACTCCGAGACGTGTTGGTGATGTGCGTC

Q   G   N   V   F   S   C   S   V   M   H   E   A   L   H   N   H   Y   T   Q   -
      AAGAGCCTCTCCCTGTCTCCGGGTAAAGTACCGATCCAGAAAGTTCAGGACGACACCAAA
661   ---------+---------+---------+---------+---------+---------+ 720
      TTCTCGGAGAGGGACAGAGGCCCATTTCATGGCTAGGTCTTTCAAGTCCTGCTGTGGTTT

K   S   L   S   L   S   P   G   K   V   P   I   Q   K   V   Q   D   D   T   K   -
      ACCTTAATTAAAACGATCGTTACGCGTATCAACGACATCAGTCACACCCAGTCGGTGAGC
721   ---------+---------+---------+---------+---------+---------+ 780
      TGGAATTAATTTTGCTAGCAATGCGCATAGTTGCTGTAGTCAGTGTGGGTCAGCCACTCG

T   L   I   K   T   I   V   T   R   I   N   D   I   S   H   T   Q   S   V   S   -
      TCTAAACAGAAAGTTACAGGCCTGGACTTCATCCCGGGTCTGCACCCGATCCTGACCTTG
781   ---------+---------+---------+---------+---------+---------+ 840
      AGATTTGTCTTTCAATGTCCGGACCTGAAGTAGGGCCCAGACGTGGGCTAGGACTGGAAC

S   K   Q   K   V   T   G   L   D   F   I   P   G   L   H   P   I   L   T   L   -
      TCCAAAATGGACCAGACCCTGGCTGTATACCAGCAGATCTTAACCTCCATGCCGTCCCGT
841   ---------+---------+---------+---------+---------+---------+ 900
      AGGTTTTACCTGGTCTGGGACCGACATATGGTCGTCTAGAATTGGAGGTACGGCAGGGCA

S   K   M   D   Q   T   L   A   V   Y   Q   Q   I   L   T   S   M   P   S   R   -
      AACGTTATCCAGATCTCTAACGACCTCGAGAACCTTCGCGACCTGCTGCACGTGCTGGCA
901   ---------+---------+---------+---------+---------+---------+ 960
      TTGCAATAGGTCTAGAGATTGCTGGAGCTCTTGGAAGCGCTGGACGACGTGCACGACCGT

N   V   I   Q   I   S   N   D   L   E   N   L   R   D   L   L   H   V   L   A   -
      TTCTCCAAATCCTGCCACCTGCCATGGGCTTCAGGTCTTGAGACTCTGGACTCTCTGGGC
961   ---------+---------+---------+---------+---------+---------+ 1020
      AAGAGGTTTAGGACGGTGGACGGTACCCGAAGTCCAGAACTCTGAGACCTGAGAGACCCG

F   S   K   S   C   H   L   P   W   A   S   G   L   E   T   L   D   S   L   G   -
      GGGGTCCTGGAAGCATCCGGTTACAGCACCGAAGTTGTTGCTCTGTCCCGTCTGCAGGGT
1021  ---------+---------+---------+---------+---------+---------+ 1080
      CCCCAGGACCTTCGTAGGCCAATGTCGTGGCTTCAACAACGAGACAGGGCAGACGTCCCA

```
        TCCCTTCAGGACATGCTTTGGCAGCTGGACCTGTCTCCGGGTTGTTAATGGATCC
1081    ----------+---------+---------+---------+---------+----- 1135
        AGGGAAGTCCTGTACGAAACCGTCGACCTGGACAGAGGCCCAACAATTACCTAGG

S  L  Q  D  M  L  W  Q  L  D  L  S  P  G  C  *
```

OB FUSION PROTEIN COMPOSITIONS AND METHODS

CROSS-REFERENCE TO RELATED APPLICATIONS

This application is a continuation of U.S. application Ser. No. 11/054,085 filed Feb. 8, 2005, now U.S. Pat. No. 7,112,659, which is a continuation of U.S. application Ser. No. 10/679,999 filed Oct. 6, 2003, now U.S. Pat. No. 6,936,439, which is a continuation of U.S. application Ser. No. 09/568,528 filed May 9, 2000, and now abandoned, which is a continuation of U.S. application Ser. No. 09/267,517, filed Mar. 12, 1999, and now abandoned, which is a continuation of U.S. application Ser. No. 08/770,973 filed Dec. 20, 1996, and now abandoned. U.S. application Ser. No. 09/568,528 is also a continuation-in-part of U.S. application Ser. No. 09/094,931 filed Jun. 15, 1998, and now abandoned, which is a continuation of U.S. application Ser. No. 09/056,719 filed Apr. 7, 1998, and now abandoned, which is a continuation of U.S. application Ser. No. 08/561,732 filed Nov. 22, 1995, and now abandoned. The applications and patents mentioned above are hereby incorporated by reference in their entireties.

FIELD OF THE INVENTION

The present invention relates to Fc-OB fusion protein compositions and methods for preparation and use thereof.

BACKGROUND

Although the molecular basis for obesity is largely unknown, the identification of the "OB gene" and protein encoded ("OB protein" or "leptin") has shed some light on mechanisms the body uses to regulate body fat deposition. See, PCT publication, WO 96/05309 (Dec. 22, 1996), Friedman et al.; Zhang et al., Nature 372: 425-432 (1994); see also, the Correction at Nature 374: 479 (1995). The OB protein is active in vivo in both ob/ob mutant mice (mice obese due to a defect in the production of the OB gene product) as well as in normal, wild type mice. The biological activity manifests itself in, among other things, weight loss. See generally, Barrinaga, "Obese" Protein Slims Mice, Science 269: 475-456 (1995). The OB protein, derivatives and use thereof as modulators for the control of weight and adiposity of animals, including mammals and humans, has been disclosed in greater detail in PCT publication WO 96/05309 (Dec. 22, 1996), hereby incorporated by reference, including figures.

The other biological effects of OB protein are not well characterized. It is known, for instance, that in ob/ob mutant mice, administration of OB protein results in a decrease in serum insulin levels, and serum glucose levels. It is also known that administration of OB protein results in a decrease in body fat. This was observed in both ob/ob mutant mice, as well as non-obese normal mice. Pelleymounter et al., Science 269: 540-543 (1995); Halaas et al., Science 269: 543-546 (1995). See also, Campfield et al., Science 269: 546-549 (1995) (Peripheral and central administration of microgram doses of OB protein reduced food intake and body weight of ob/ob and diet-induced obese mice but not in db/db obese mice.) In none of these reports have toxicity's been observed, even at the highest doses.

Despite the promise of clinical application of the OB protein, the mode of action of the OB protein in vivo is not clearly elucidated. Information on the OB receptor, shows high affinity binding of the OB protein detected in the rat hypothalamus, which indicates OB receptor location. Stephens et al., Nature 377: 530-532. The db/db mouse displays the identical phenotype as the ob/ob mouse, i.e., extreme obesity and Type II diabetes; this phenotype is thought to be due to a defective OB receptor, particularly since db/db mice fail to respond to OB protein administration. See Stephens et al., supra.

With the advances in recombinant DNA technologies, the availability of recombinant proteins for therapeutic use has engendered advances in protein formulation and chemical modification. One goal of such modification is protein protection and decreased degradation. Fusion proteins and chemical attachment may effectively block a proteolytic enzyme from physical contact with the protein backbone itself, and thus prevent degradation. Additional advantages include, under certain circumstances, increasing the stability, circulation time, and the biological activity of the therapeutic protein. A review article describing protein modification and fusion proteins is Francis, Focus on Growth Factors 3:4-10 (May 1992) (published by Mediscript, Mountview Court, Friern Barnet Lane, London N20, OLD, UK).

One such modification is the use of the Fc region of immunoglobulins. Antibodies comprise two functionally independent parts, a variable domain known as "Fab", which binds antigen, and a constant domain, known as "Fc" which provides the link to effector functions such as complement or phagocytic cells. The Fc portion of an immunoglobulin has a long plasma half-life, whereas the Fab is short-lived. Capon, et al., Nature 337: 525-531 (1989).

Therapeutic protein products have been constructed using the Fc domain to provide longer half-life or to incorporate functions such as Fc receptor binding, protein A binding, complement fixation and placental transfer which all reside in the Fc proteins of immunoglobulins. Id. For example, the Fc region of an IgG1 antibody has been fused to the N-terminal end of CD30-L, a molecule which binds CD30 receptors expressed on Hodgkin's Disease tumor cells, anaplastic lymphoma cells, T-cell leukemia cells and other malignant cell types. See, U.S. Pat. No. 5,480,981. IL-10, an antiinflammatory and antirejection agent has been fused to murine Fcγ2a in order to increase the cytokine's short circulating half-life. Zheng, X. et al., The Journal of Immunology, 154: 5590-5600 (1995). Studies have also evaluated the use of tumor necrosis factor receptor linked with the Fc protein of human IgG1 to treat patients with septic shock. Fisher, C. et al., N. Engl. J. Med., 334: 1697-1702 (1996); Van Zee, K. et al., The Journal of Immunology, 156: 2221-2230 (1996). Fc has also been fused with CD4 receptor to produce a therapeutic protein for treatment of AIDS. See, Capon et al., Nature, 337:525-531 (1989). In addition, the N-terminus of interleukin 2 has also been fused to the Fc portion of IgG1 or IgG3 to overcome the short half life of interleukin 2 and its systemic toxicity. See, Harvill et al., Immunotechnology, 1: 95-105 (1995).

Due to the identification of the OB protein as a promising therapeutic protein, there exists a need to develop OB analog compositions for clinical application in conjunction with or in place of OB protein administration. Such development would include OB analog compositions where protein formulations and chemical modifications achieve decreased protein degradation, increased stability and circulation time. The present invention provides such compositions.

SUMMARY OF THE INVENTION

The present invention relates to Fc-OB fusion protein compositions, methods of preparation of such compositions and uses thereof. In particular, the present invention relates to a genetic fusion protein comprising the Fc region or analogs of immunoglobulins fused to the N-terminal portion of the OB protein or analogs. The Fc-OB fusion protein is capable of dimerizing via the cysteine residues of the Fc region. Unexpectedly, genetic fusion modification with Fc at the N-terminus of the OB protein demonstrates advantages in stability, clearance rate and decreased degradation which are not seen in OB protein or with fusion of Fc to the C-terminus of the OB protein. Surprisingly and importantly, the N-terminus modification provides unexpected protein protection from degradation, increases circulation time and stability, when compared to the OB protein or Fc modification to the OB protein C-terminus. Such unexpected advantages from the Fc modification to OB protein would be advantageous to OB protein consumers, in that these changes contribute to lower doses required or less frequent dosing. Thus, as described below in more detail, the present invention has a number of aspects relating to the genetic modification of proteins via fusion of the Fc region to the OB protein (or analogs thereof), as well as, specific modifications, preparations and methods of use thereof.

Accordingly, in one aspect, the present invention provides a Fc-OB fusion protein wherein Fc is genetically fused to the N-terminus of the OB protein (or analogs thereof). In addition, the Fc portion may also be linked to the N-terminus of the OB protein (or analogs thereof) via peptide or chemical linkers as known in the art. As noted above and described in more detail below, the Fc-OB fusion protein has unexpected protections from degradation and increased circulation time and stability when compared to the OB protein or C-terminus OB-Fc fusion proteins. Additional aspects of the present invention, therefore, include not only Fc-OB fusion protein compositions, but also DNA sequences encoding such proteins, related vectors and host cells containing such vectors, both useful for producing fusion proteins of the present invention.

In a second aspect, the present invention provides for preparing the Fc-OB fusion protein. Such methods include recombinant DNA techniques for preparation of recombinant proteins. Furthermore, such aspects include methods of fermentation and purification as well.

In another aspect, the present invention provides methods for treating excess weight in an individual or animals, including modulation of and/or fat deposition by the administration of Fc-OB fusion proteins. Due to the Fc-OB fusion protein characteristics, methods are contemplated which reduce the amount and/or frequency of dosage of OB protein by using Fc-OB weight reducing agent.

In yet another aspect, the present invention provides for therapies for the treatment of co-morbidities associated with excess fat, such as diabetes, dys- or hyperlipidemias, arterial sclerosis, arterial plaque, the reduction or prevention of gall stones formation, stoke, and also an increase in insulin sensitivity and/or an increase in lean tissue mass.

In another aspect, the present invention also provides for related pharmaceutical compositions of the Fc-OB proteins, analogs and derivatives thereof, for use in the above therapies.

BRIEF DESCRIPTION OF THE DRAWINGS

FIG. 1 Recombinant murine metOB (double stranded) DNA (SEQ. ID. NOs.: 1 and 2) and amino acid sequence (SEQ. ID. NO. 3).

FIG. 2 Recombinant human metOB analog (double stranded) DNA (SEQ. ID. NOs.: 4 and 5) and amino acid sequence (SEQ. ID. NO. 6).

FIG. 3(A-C) Recombinant human metFc-OB (double stranded) DNA (SEQ. ID. NOs.: 7 and 8) and amino acid sequence (SEQ. ID. NO. 9).

FIG. 4(A-C) Recombinant human metFc-OB variant (double stranded) DNA (SEQ. ID. NOs.: 10 and 11) and amino acid sequence (SEQ. ID. NO. 12).

FIG. 5(A-C) Recombinant human metFc-OB variant (double stranded) DNA (SEQ. ID. NOs.: 13 and 14) and amino acid sequence (SEQ. ID. NO. 15).

FIG. 6(A-C) Recombinant human metFc-OB variant (double stranded) DNA (SEQ. ID. NOs.: 16 and 17) and amino acid sequence (SEQ. ID. NO. 18).

DETAILED DESCRIPTION

The present invention relates to Fc-OB fusion protein compositions, methods of preparation of such compositions and uses thereof. In particular, the present invention relates to the genetic or chemical fusion of the Fc region of immunoglobulins to the N-terminal portion of the OB protein. Unexpectedly, fusion of Fc at the N-terminus of the OB protein demonstrates advantages which are not seen in OB protein or with fusion of Fc at the C-terminus of the OB protein. Surprisingly, the N-terminally modified Fc-OB protein provides unexpected protein protection from degradation, increased circulation time and increased stability. Accordingly, the Fc-OB fusion protein, and analogs or derivatives thereof, as well as, related methods of use and preparation, are described in more detail below.

Compositions

The Fc sequence of the recombinant human Fc-OB sequence set forth in SEQ. ID. NO. 9 (See FIG. 3) may be selected from the human immunoglobulin IgG-1 heavy chain, see Ellison, J. W. et al., Nucleic Acids Res. 10: 4071-4079 (1982), or any other Fc sequence known in the art (e.g. other IgG classes including but not limited to IgG-2, IgG-3 and IgG-4, or other immunoglobulins). Variant, analogs or derivatives of the Fc portion may be constructed by, for example, making various substitutions of residues or sequences.

Cysteine residues can be deleted or replaced with other amino acids to prevent formation of disulfide crosslinks of the Fc sequences. In particular amino acid at position 5 of SEQ. ID. NO. 9 is a cysteine residue. The recombinant Fc-OB sequence of SEQ. ID. NO. 9 is a 378 amino acid Fc-OB protein (not counting the methionine residue). The first amino acid sequence for the recombinant Fc-OB protein of FIG. 3 is referred to as +1 with the methionine at the −1 position.

One may remove the cysteine residue at position 5 or substitute it with one or more amino acids. An alanine residue may be substituted for the cysteine residue at position 6 giving the variant amino acid sequence of FIG. 4 (SEQ. ID. NO. 12). The recombinant Fc-OB protein of FIG. 4 is a 378 amino acid Fc-OB protein (not counting the methionine residue). The first amino acid sequence for the recombinant Fc-OB protein of FIG. 4 is referred to as +1 with the methionine at the −1 position.

Likewise, the cysteine at position 5 of SEQ. ID. NO. 9 could be substituted with a serine or other amino acid residue or deleted. A variant or analog may also be prepared by deletion of amino acids at positions 1, 2, 3, 4 and 5 as with the variant in SEQ. ID. NO. 15 (See FIG. 5). Substitutions at these positions can also be made and are with in the scope of this invention. The recombinant Fc-OB protein of FIG. 5 is a 373 amino acid Fc-OB protein (not counting the methionine residue). The first amino acid sequence for the recombinant Fc-OB protein of FIG. 5 is referred to as +1 with the methionine at the −1 position.

Modifications may also be made to introduce four amino acid substitutions to ablate the Fc receptor binding site and the complement (C1q) binding site. These variant modifications from SEQ. ID. NO. 15 would include leucine at position 15 substituted with glutamate, glutamate at position 98 substituted with alanine, and lysines at positions 100 and 102 substituted with alanines (see FIG. 6 and SEQ. ID. NO. 18). The recombinant Fc-OB protein of FIG. 6 is a 373 amino acid Fc-OB protein (not counting the methionine residue). The first amino acid sequence for the recombinant Fc-OB protein of FIG. 6 is referred to as +1 with the methionine at the −1 position.

Likewise, one or more tyrosine residues can be replaced by phenylalanine residues as well. In addition, other variant amino acid insertions, deletions and/or substitutions are also contemplated and are within the scope of the present invention. Furthermore, alterations may be in the form of altered amino acids, such as peptidomimetics or D-amino acids. The Fc protein may also be linked to the OB proteins of the Fc-OB protein by "linker" moieties whether chemical or amino acids of varying lengths. Such chemical linkers are well known in the art. Amino acid linker sequences can include but are not limited to:
  (a) ala-ala-ala;
  (b) ala-ala-ala-ala (SEQ ID NO:19);
  (c) ala-ala-ala-ala-ala (SEQ ID NO:20);
  (d) gly-gly;
  (e) gly-gly-gly;
  (f) gly-gly-gly-gly-gly (SEQ ID NO:21);
  (g) gly-gly-gly-gly-gly-gly-gly (SEQ ID NO:22);
  (h) gly-pro-gly;
  (i) gly-gly-pro-gly-gly (SEQ ID NO:23); and
  (j) any combination of subparts (a) through (i).

The OB portion of the Fc-OB fusion protein may be selected from the recombinant murine set forth in SEQ. ID. NO. 3 (See FIG. 1), or the recombinant human protein as set forth in Zhang et al., Nature, supra, (herein incorporated by reference) or those lacking a glutaminyl residue at position 28. (See Zhang et al, Nature, supra, at page 428.) One may also use the recombinant human OB protein analog as set forth in SEQ. ID. NO. 6 (See FIG. 2), which contains: (1) an arginine in place of lysine at position 35; and (2) a leucine in place of isoleucine at position 74. (A shorthand abbreviation for this analog is the recombinant human R->L$^{35}$, I->L$^{74}$). The amino acid sequences for the recombinant human and recombinant murine proteins or analogs with or without the fused Fc portion at the N-terminus of the OB protein are set forth below with a methionyl residue at the −1 position; however, as with any of the present OB proteins and analogs, the methionyl residue may be absent.

The murine protein is substantially homologous to the human protein, particularly as a mature protein, and, further, particularly at the N-terminus. One may prepare an analog of the recombinant human protein by altering (such as substituting amino acid residues), in the recombinant human sequence, the amino acids which diverge from the murine sequence. Because the recombinant human protein has biological activity in mice, such an analog would likely be active in humans. For example, using a human protein having a lysine at residue 35 and an isoleucine at residue 74 according to the numbering of SEQ. ID. NO. 6, wherein the first amino acid is valine, and the amino acid at position 146 is cysteine, one may substitute with another amino acid one or more of the amino acids at positions 32, 35, 50, 64, 68, 71, 74, 77, 89, 97, 100, 105, 106, 107, 108, 111, 118, 136, 138, 142, and 145. One may select the amino acid at the corresponding position of the murine protein, (SEQ. ID. NO. 3), or another amino acid.

One may further prepare "consensus" molecules based on the rat OB protein sequence. Murakami et al., Biochem. Biophys. Res. Comm. 209: 944-952 (1995) herein incorporated by reference. Rat OB protein differs from human OB protein at the following positions (using the numbering of SEQ. ID. NO. 6): 4, 32, 33, 35, 68, 71, 74, 77, 78, 89, 97, 100, 101, 102, 105, 106, 107, 108, 111, 118, 136, 138 and 145. One may substitute with another amino acid one or more of the amino acids at these divergent positions. The positions in bold print are those in which the murine OB protein as well as the rat OB protein are divergent from the human OB protein, and thus, are particularly suitable for alteration. At one or more of a positions, one may substitute an amino acid from the corresponding rat OB protein, or another amino acid.

The positions from both rat and murine OB protein which diverge from the mature human OB protein are: 4, 32, 33, 35, 50, 64, 68, 71, 74, 77, 78, 89, 97, 100, 102, 105, 106, 107, 108, 111, 118, 136, 138, 142, and 145. An OB protein according to SEQ. ID. NO. 6 having one or more of the above amino acids replaced with another amino acid, such as the amino acid found in the corresponding rat or murine sequence, may also be effective.

In addition, the amino acids found in rhesus monkey OB protein which diverge from the mature human OB protein are (with identities noted in parentheses in one letter amino acid abbreviation): 8 (S), 35 (R), 48(V), 53(Q), 60(I), 66(I), 67(N), 68((L), 89(L), 100(L), 108(E), 112 (D), and 118 (L). Since the recombinant human OB protein is active in cynomolgus monkeys, a human OB protein according to SEQ. ID. NO. 6 (with lysine at position 35 and isoleucine at position 74) having one or more of the rhesus monkey divergent amino acids replaced with another amino acid, such as the amino acids in parentheses, may be effective. It should be noted that certain rhesus divergent amino acids are also those found in the above murine species (positions 35, 68, 89, 100 and 112). Thus, one may prepare a murine/rhesus/human consensus molecule having (using the numbering of SEQ. ID. NO. 6 having a lysine at position 35 and an isoleucine at position 74) having one or more of the amino acids at positions replaced by another amino acid: 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145.

Other analogs may be prepared by deleting a part of the protein amino acid sequence. For example, the mature protein lacks a leader sequence (−22 to −1). One may prepare the following truncated forms of human OB protein molecules (using the numbering of SEQ. ID. NO. 6):
  (a) amino acids 98-146
  (b) amino acids 1-32
  (c) amino acids 40-116
  (d) amino acids 1-99 and (connected to) 112-146
  (e) amino acids 1-99 and (connected to) 112-146 having one or more of amino acids 100-111 placed between amino acids 99 and 112.

In addition, the truncated forms may also have altered one or more of the amino acids which are divergent (in the rat, murine, or rhesus OB protein) from human OB protein. Furthermore, any alterations may be in the form of altered amino acids, such as peptidomimetics or D-amino-acids.

Therefore, the present invention encompasses a Fc-OB fusion protein wherein the OB protein is selected from:
  (a) the amino acid sequence 1-146 as set forth in SEQ. ID. NO. 3 (below) or SEQ. ID. NO. 6;
  (b) the amino acid sequence 1-146 as set forth in SEQ. ID. NO. 6 having a lysine residue at position 35 and an isoleucine residue at position 74;
  (c) the amino acid sequence of subpart (b) having a different amino acid substituted in one or more of the following positions (using the numbering according to SEQ.

ID. NO. 6 and retaining the same numbering even in the absence of a glutaminyl residue at position 28): 4, 32, 33, 35, 50, 64, 68, 71, 74, 77, 78, 89, 97, 100, 102, 105, 106, 107, 108, 111, 118, 136, 138, 142, and 145;

(d) the amino acid sequence of subparts (a), (b) or (c) optionally lacking a glutaminyl residue at position 28;

(e) the amino acid sequence of subparts (a), (b), (c), or (d) having a methionyl residue at the N-terminus;

(f) a truncated OB protein analog selected from among: (using the numbering of SEQ. ID. NO. 6):
  (i) amino acids 98-146
  (ii) amino acids 1-32
  (iii) amino acids 40-116
  (iv) amino acids 1-99 and 112-146
  (v) amino acids 1-99 and 112-146 having one or more of amino acids 100-111 placed between amino acids 99 and 112; and,
  (vi) the truncated OB analog of subpart (i) having one or more of amino acids 100, 102, 105, 106, 107, 108, 111, 118, 136, 138, 142, and 145 substituted with another amino acid;
  (vii) the truncated analog of subpart (ii) having one or more of amino acids 4, 8 and 32 substituted with another amino acid;
  (viii) the truncated analog of subpart (iii) having one or more of amino acids 50, 53, 60, 64, 66, 67, 68, 71, 74, 77, 78, 89, 97, 100, 102, 105, 106, 107, 108, 111 and 112 replaced with another amino acid;
  (vix) the truncated analog of subpart (iv) having one or more of amino acids 4, 8, 32, 33, 35, 48, 50, 53, 60, 64, 66, 67, 68, 71, 74, 77, 78, 89, 97, 112, 118, 136, 138, 142, and 145 replaced with another amino acid; and
  (x) the truncated analog of subpart (v) having one or more of amino acids 4, 32, 33, 35, 50, 64, 68, 71, 74, 77, 78, 89, 97, 100, 102, 105, 106, 107, 108, 111, 118, 136, 138, 142, and 145 replaced with another amino acid;
  (xi) the truncated analog of any of subparts (i)-(x) having an N-terminal methionyl residue; and (g) the OB protein or analog derivative of any of subparts (a) through (f) comprised of a chemical moiety connected to the protein moiety;

(h) a derivative of subpart (g) wherein said chemical moiety is a water soluble polymer moiety;

(i) a derivative of subpart (h) wherein said water soluble polymer moiety is polyethylene glycol;

(j) a derivative of subpart (h) wherein said water soluble polymer moiety is a polyaminoacid moiety;

(k) a derivative of subpart (h) through (j) wherein said moiety is attached at solely the N-terminus of said protein moiety; and (l) an OB protein, analog or derivative of any of subparts (a) through (k) in a pharmaceutically acceptable carrier.

Derivatives

The present Fc-OB fusion proteins (herein the term "protein" is used to include "peptide," Fc, OB or analogs, such as those recited infra, unless otherwise indicated) are derivatized by the attachment of one or more chemical moieties to the Fc-OB fusion protein moiety. These chemically modified derivatives may be further formulated for intraarterial, intraperitoneal, intramuscular subcutaneous, intravenous, oral, nasal, pulmonary, topical or other routes of administration as discussed below. Chemical modification of biologically active proteins has been found to provide additional advantages under certain circumstances, such as increasing the stability and circulation time of the therapeutic protein and decreasing immunogenicity. See, U.S. Pat. No. 4,179,337, Davis et al., issued Dec. 18, 1979. For a review, see Abuchowski et al., in Enzymes as Drugs. (J. S. Holcerberg and J. Roberts, eds. pp. 367-383 (1981)); Francis et al., supra.

The chemical moieties suitable for such derivatization may be selected from among various water soluble polymers. The polymer selected should be water soluble so that the protein to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the present proteins and peptides, the effectiveness of the derivatization may be ascertained by administering the derivative, in the desired form (i.e., by osmotic pump, or, more preferably, by injection or infusion, or, further formulated for oral, pulmonary or nasal delivery, for example), and observing biological effects as described herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrolidone, poly-1,3-dioxolane, poly-1,3,6-trioxane, ethylene/maleic anhydride copolymer, polyaminoacids (either homopolymers or random copolymers), and dextran or poly(n-vinyl pyrolidone)polyethylene glycol, propylene glycol homopolymers, polypropylene oxide/ethylene oxide co-polymers, polyoxyethylated polyols and polyvinyl alcohol. Polyethylene glycol propionaldenhyde may have advantages in manufacturing due to its stability in water. Also, succinate and styrene may also be used.

The OB or Fc proteins used to formulate the Fc-OB fusion protein, may be prepared by attaching polyaminoacids or branch point amino acids to the Fc or OB protein (or analogs) moiety. For example, the polyaminoacid may be an additional carrier protein which, like the Fc fused to the OB protein or OB analog of the present invention, serves to also increase the circulation half life of the protein in addition to the advantages achieved via the Fc-OB fusion protein above. For the present therapeutic or cosmetic purpose of the present invention, such polyaminoacids should be those which have or do not create neutralizing antigenic response, or other adverse responses. Such polyaminoacids may be selected from the group consisting of serum album (such as human serum albumin), an additional antibody or portion thereof (e.g. the Fc region), or other polyaminoacids, e.g. lysines. As indicated below, the location of attachment of the polyaminoacid may be at the N-terminus of the Fc-OB protein moiety, or C-terminus, or other places in between, and also may be connected by a chemical "linker" moiety to the Fc-OB protein.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The chemical moieties should be attached to the protein with consideration of effects on functional or antigenic domains of the protein. There are a number of attachment methods available to those skilled in the art. E.g., EP 0 401 384 herein incorporated by reference (coupling PEG to G-CSF), see also Malik et al., Exp. Hematol. 20: 1028-1035 (1992) (reporting pegylation of GH-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

One may specifically desire N-terminally chemically modified Fc-OB fusion protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the $\epsilon$-amino group of the lysine residues and that of the $\alpha$-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

An N-terminally monopegylated derivative is preferred for ease in production of a therapeutic. N-terminal pegylation ensures a homogenous product as characterization of the product is simplified relative to di-, tri- or other multi-pegylated products. The use of the above reductive alkylation process for preparation of an N-terminal product is preferred for ease in commercial manufacturing.

Complexes

The Fc-OB fusion protein, analog or derivative thereof may be administered complexed to a binding composition. Such binding composition may have the effect of prolonging the circulation time even further than that achieved with the Fc-OB fusion protein, analog or derivative. Such composition may be a protein (or synonymously, peptide). An example of a binding protein is OB protein receptor or portion thereof, such as a soluble portion thereof. Other binding proteins may be ascertained by examining OB protein or Fc-OB protein in serum, or by empirically screening for the presence of binding. Binding proteins used will typically not interfere with the ability of OB protein, Fc-OB fusion proteins, or analogs or derivatives thereof, to bind to endogenous OB protein receptor and/or effect signal transduction.

Pharmaceutical Compositions

The present invention also provides methods of using pharmaceutical compositions of the Fc-OB fusion proteins and derivatives. Such pharmaceutical compositions may be for administration for injection, or for oral, pulmonary, nasal, transdermal or other forms of administration. In general, comprehended by the invention are pharmaceutical compositions comprising effective amounts of protein or derivative products of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the Fc-OB fusion protein (or analog or derivative), and inert ingredients which allow for protection against the stomach environment, and release of the biologically active material in the intestine.

Also specifically contemplated are oral dosage forms of the above derivatized proteins. Fc-OB fusion protein may be chemically modified so that oral delivery of the derivative is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: Polyethylene glycol, copolymers of ethylene glycol and propylene glycol, carboxymethyl cellulose, dextran, polyvinyl alcohol, polyvinyl pyrrolidone and polyproline. Abuchowski and Davis, Soluble Polymer-Enzyme Adducts. In: "Enzymes as Drugs", Hocenberg and Roberts, eds., Wiley-Interscience, New York, N.Y., (1981), pp 367-383; Newmark; at al., J. Appl. Biochem. 4: 185-189 (1982). Other polymers that could be used are poly-1,3-dioxolane and poly-1,3,6-tioxocane. Preferred for pharmaceutical usage, as indicated above, are polyethylene glycol moieties.

For the Fc-OB fusion protein, analog or derivative, the location of release may be the stomach, the small intestine (e.g., the duodenum, jejunum, or ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the Fc-OB fusion protein, analog or derivative, or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include ionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

Controlled release formulation may be desirable. The drug could be incorporated into an inert matrix which permits release by either diffusion or leaching mechanisms e.g., gums. Slowly degenerating matrices may also be incorporated into the formulation, e.g., alginates, polysaccharides. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharmaceutical Research 7: 565-569 (1990); Adjei et al., International Journal of Pharmaceutics 63: 135-144 (1990) (leuprolide acetate); Braquet et al., Journal of Cardiovascular Pharmacology 13 (suppl. 5): s.143-146 (1989) (endothelin-1); Hubbard et al., Annals of Internal Medicine 3: 206-212 (1989) ($\alpha$1-antitrypsin); Smith et al., J. Clin. Invest. 84: 1145-1146 (1989) ($\alpha$-1-proteinase); Oswein et al., "Aerosolization of Proteins", Proceedings of Symposium on Respiratory Drug Delivery II, Keystone, Colo., March, 1990 (recombinant human growth hormone); Debs et al., The Journal of Immunology 140: 3482-3488 (1988) (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of protein (or analog or derivative). Typically, each formulation is specific to the type of device employed and may involve the use of an appropriate propellant material, in addition to diluents, adjuvants and/or carriers useful in therapy.

The protein (or derivative) should most advantageously be prepared in particulate form with an average particle size of less than 10 $\mu$m (or microns), most preferably 0.5 to 5 $\mu$m, for most effective delivery to the distal lung.

Carriers include carbohydrates such as trehalose, mannitol, xylitol, sucrose, lactose, and sorbitol. Other ingredients for use in formulations my include DPPC, DOPE, DSPC and DOPC. Natural or synthetic surfactants may be used. Polyethylene glycol may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise Fc-OB protein, analogs or derivatives thereof, dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery of the protein (or analog or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucus membranes is also contemplated.

Dosage

One skilled in the art will be able to ascertain effective dosages by administration and observing the desired therapeutic effect. Due to the N-terminus modification of the OB protein, the present invention provides unexpected protein protection from degradation, and increases circulation time and stability, when compared to OB protein or C-terminus modification of the OB protein. One skilled in the art, therefore, will be able to ascertain from these changes that an effective dosage may require lower doses or less frequent dosing.

Preferably, the formulation of the molecule will be such that between about 0.10 $\mu$g/kg/day and 10 mg/kg/day will yield the desired therapeutic effect. The effective dosages may be determined using diagnostic tools over time. For example, a diagnostic for measuring the amount of OB protein or Fc-OB fusion protein in the blood (or plasma or serum) may first be used to determine endogenous levels of protein. Such diagnostic tools may be in the form of an antibody assay, such as an antibody sandwich assay. The amount of endogenous OB protein is quantified initially, and a baseline is determined. The therapeutic dosages are determined as the quantification of endogenous and exogenous OB protein or Fc-OB fusion protein (that is, protein, analog or derivative found within the body, either self-produced or administered) is continued over the course of therapy. The dosages may therefore vary over the course of therapy, with a relatively high dosage being used initially, until therapeutic benefit is seen, and lower dosages used to maintain the therapeutic benefits.

Ideally, in situations where solely reduction in blood lipid levels is desired, where maintenance of reduction of blood lipid levels is desired, or an increase in lean body mass is desired, the dosage will be insufficient to result in weight loss.

Thus, during an initial course of therapy of an obese person, dosages may be administered whereby weight loss and concomitant blood lipid level lowering or concomitant fat tissue decrease/lean mass increase is achieved. Once sufficient weight loss is achieved, a dosage sufficient to prevent re-gaining weight, yet sufficient to maintain desired blood lipid levels or lean mass increase (or, prevention of lean mass depletion) may be administered. These dosages can be determined empirically, as the effects of OB or Fc-OB protein are reversible, (e.g., Campfield et al., Science 269: 546-549 (1995) at 547). Thus, if a dosage resulting in weight loss is observed when weight loss is not desired, one would administer a lower dose in order to achieve the desired blood lipid levels or increase in lean tissue mass, yet maintain the desired weight.

For increasing an individual's sensitivity to insulin, similar dosage considerations may be taken into account. Lean mass increase without weight loss may be achieved sufficient to decrease the amount of insulin (or, potentially, amylin, thiazolidinediones, or other potential diabetes treating drugs) an individual would be administered for the treatment of diabetes.

For increasing overall strength, there may be similar dosage considerations. Lean mass increase with concomitant increase in overall strength may be achieved with doses insufficient to result in weight loss. Other benefits, such as an increase in red blood cells (and oxygenation in the blood) and a decrease in bone resorption or osteoporosis may also be achieved in the absence of weight loss.

Combinations

The present methods may be used in conjunction with other medicaments, such as those useful for the treatment of diabetes (e.g., insulin, possibly, thiazolidinediones, amylin, or antagonists thereof), cholesterol and blood pressure lowering medicaments (such as those which reduce blood lipid levels or other cardiovascular medicaments), and activity increasing medicaments (e.g., amphetamines). Appetite suppressants may also be used (such as those affecting the levels of serotonin or neuropeptide Y). Such administration may be simultaneous or may be in seriatim.

In addition, the present methods may be used in conjunction with surgical procedures, such as cosmetic surgeries designed to alter the overall appearance of a body (e.g., liposuction or laser surgeries designed to reduce body mass). The health benefits of cardiac surgeries, such as bypass surgeries or other surgeries designed to relieve a deleterious condition caused by blockage of blood vessels by fatty deposits, such as arterial plaque, may be increased with concomitant use of the present compositions and methods. Methods to eliminate gall stones, such as ultrasonic or laser methods, may also be used either prior to, during or after a course of the present therapeutic methods. Furthermore, the present methods may be used as an adjunct to surgeries or therapies for broken bones, damaged muscle, or other therapies which would be improved by an increase in lean tissue mass.

The following examples are offered to more fully illustrate the invention, but are not to be construed as limiting the scope thereof.

EXAMPLE 1

Use of Murine FC-OB Protein Via Subcutaneous Injection

This example demonstrates that injection subcutaneously of murine Fc-OB protein results in weight loss in normal mice. Normal (non-obese) CD1 mice were administered murine Fc-OB protein via subcutaneous injections over a 22 day time period. A dosage of 10 mg protein/kg body weight/day resulted in a 14% (+/−1.1%) loss from baseline weight by the 22nd day of injections. A dosage of PBS resulted in a 3.9% (+/−3.3%) loss from baseline weight by the 22nd day of injections. The weight loss with the use of 10 mg protein/kg body weight/day of Fc-OB protein in obese CD1 mice resulted in a 10% (+/−4.3%) loss from baseline weight and a dosage of PBS resulted in a 8.7% (+/−1.3%) loss from baseline weight, both by the 22nd day of injections Presented below are the percent (%) differences from baseline weight in CD1 mice (8 weeks old):

TABLE 1

Weight Loss Upon Subcutaneous Injection

| Time (days) | Vehicle (PBS) | Lean/Recombinant Fc-OB Fusion Protein | Obese/Recombinant Fc-OB Fusion Protein |
|---|---|---|---|
| 1-2 | −.44 +/− 1.1 | −3.6 +/− .41 | −1.03 +/− 1.36 |
| 3-4 | −1.07 +/− .13 | −6.8 +/− 1.5 | −2.7 +/− 1.1 |
| 5-6 | −.13 +/− 1.1 | −9.5 +/− 1.2 | −4.9 +/− .95 |
| 7-8 | −.92 +/− .29 | −12.5 +/− 1.6 | −7.7 +/− 2.9 |
| 9-10 | 1.6 +/− 1.3 | −12.6 +/− 1.9 | −8.2 +/− 2.9 |
| 11-12 | −1.98 +/− 1 | −13.6 +/− 1.96 | −8.6 +/− 2.9 |
| 13-14 | −5.2 +/− 1.3 | −14.6 +/− 1.7 | −10.1 +/− 3.6 |
| 15-16 | −8.6 +/− 0.1 | −14.5 +/− 2 | −9.4 +/− 2.2 |
| 17-18 | −8.5 +/− .64 | −16.1 +/− 1.8 | −9.6 +/− 2.99 |
| 19-20 | −4.1 +/− .99 | −16 +/− 1.5 | −10.4 +/− 3.3 |
| 21-22 | −3.9 +/− 3.3 | −14.1 +/− 1.1 | −10 +/− 4.3 |

As can be seen, at the end of a 22 day subcutaneous regime, animals receiving the FC-OB protein lost over 14.1% of their body weight in lean and 10% of body weight in obese, as compared to animals only receiving the PBS vehicle and as compared to baseline.

Surprisingly, animals receiving Fc-OB protein up to 22 days continued to loose weight up until 28 days, 4 days after the last injection. Normal (non-obese) CD1 mice administered 10 mg protein/kg body weight/day of murine Fc-OB protein via subcutaneous injections stopped at day 22 resulted in a 21% loss from baseline weight at day 28 as compared to 14% loss at day 22. Likewise, obese CD1 mice administered 10 mg protein/kg body weight/day of murine Fc-OB protein stopped at day 22 resulted in a 13% loss from baseline weight at day 28 compared to 10% loss at day 22. At day 34 weight loss was maintained at 10% loss in obese mice where lean mice recovered to 5% loss. Controls in each system from day 22 through day 34 averaged from 4% in obese mice and 7% gain in lean mice.

EXAMPLE 2

Use of Human FC-OB Protein Via Subcutaneous Injection in C57 Mice

This example demonstrates that injection subcutaneously of human Fc-OB protein results in weight loss in normal mice. Normal (non-obese) C57 mice were administered human Fc-OB protein via subcutaneous injections over a 7 day time period. A dosage of 10 mg protein/kg body weight/day resulted in a 12% (+/−1.3%) loss from baseline weight by the 7th day of injections. A dosage of 1 mg protein/kg body weight/day resulted in a 8.9% (+/−1.5%) loss from baseline weight by the 7th day of injections. The weight loss with the use of 10 mg protein/kg body weight/day of human OB protein in obese C57 mice resulted in a 1.1% (+/−0.99%) loss from baseline weight and a dosage of 1 mg protein/kg body weight/day resulted in a 2.5% (+/−1.1%) loss from baseline weight, both by the 7th day of injections.

Results

Presented below are the percent (%) differences from baseline weight in C57 mice (8 weeks old):

TABLE 2

Weight Loss Upon Subcutaneous Injection

| Time (days) | Vehicle (PBS) | Recombinant Fc-OB Fusion Protein | Recombinant OB Protein |
|---|---|---|---|
| 1-2 | .258 +/− 1.3 | −6.4 +/− 1.6 | −2.1 +/− .91 |
| 3-4 | 2.2 +/− 1.1 | −12.1 +/− 1.5 | −.78 +/− .36 |
| 5-6 | 4.5 +/− 2 | −11.5 +/− 1.5 | −1.7 +/− .6 |
| 7-8 | 7.0 +/− 2.1 | −11.9 +/− 1.6 | 0.1 +/− 1.2 |
| 9-10 | 9.0 +/− 1.9 | −11.5 +/− 1.3 | 7.2 +/− 2.7 |
| 11-12 | 10 +/− 3.8 | −9 +/− 1.4 | 10.9 +/− 2.9 |
| 13-14 | 12.5 +/− 4.4 | −9.5 +/− 1.6 | 12.3 +/− 6.4 |
| 15-16 | 11.1 +/− 1.0 | −3.0 +/− 1.5 | 10.3 +/− 3.3 |
| 17-18 | 17.2 +/− 3.6 | 8.0 +/− 1.3 | 13.3 +/− 3.4 |

As can be seen, at the end of a day 17 after a 7 day subcutaneous regime at 10 mg/kg/day, animals receiving the FC-OB protein recovered to 8% of their body weight. Animals receiving dosages of 1 mg/kg/day after a 7 day subcutaneous regime returned to 6.4% of body weight after 12 days.

These studies also show that during recovery periods from day 7 to day 22, after the last injection at day 7, body weight recovery is slower in the Fc-OB treated C57 mice that with the OB treated mice. This suggests that the Fc-OB protein is not cleared as quickly as OB protein thereby causing the extended weight loss effect.

EXAMPLE 3

Dose Response of CF7 Mice Treated with Fc-OB Fusion Protein

An additional study demonstrated that there was a dose response to continuous administration of Fc-OB protein. In this study, obese CF7 mice, weighing 35-40 g were administered recombinant human Fc-OB protein using methods similar to the above example. The results are set forth in Table 3, below, (with % body weight lost as compared to baseline, measured as above):

TABLE 3

Dose Response With Continuous Administration

| Dose | Time | % Reduction in Body Weight |
|---|---|---|
| 0.25 mg/kg/day | Day 5 | 4 |
| 0.5 mg/kg/day | Day 5 | 12 |
| 1 mg/kg/day | Day 5 | 16 |

As can be seen, increasing the dose from 0.25 mg/kg/day to 1 mg/kg/day increased the weight lost from 4% to 16%. It is also noteworthy that at day 5, the 1 mg/kg/day dosage resulted in a 16% reduction in body weight. These studies also showed slow weight recovery rates to 0% suggesting that the Fc-OB protein is not quickly cleared thereby causing the extended weight lose effect.

EXAMPLE 4

Pharmacokinetics of Recombinant Human Fc-OB in CD-1 Mice and Dogs

This study demonstrated the pharmacokinetic properties of recombinant human met Fc-OB protein in CD-1 mice and dogs. Following intravenous or subcutaneous dosing at 1 mg/kg/day, serum concentrations of recombinant human met Fc-OB protein and human met OB protein were determined by an enzyme-linked immunosorbent assay (ELISA).

In both species, an increase in exposure, as quantified by higher peak serum concentrations and larger areas under-the-serum-concentration-curve (AUC), was observed when compared to recombinant met-human OB protein. Fc-OB has lower systemic clearance than recombinant met-human OB protein. This is seen in the lower clearance and longer half-life of Fc-OB over OB protein. The increase in size causes not only an increase in protein stability, but also a decrease in the efficiency of renal clearance. As a result, Fc-OB is cleared slower from the systemic circulation. The increases in peak time, peak serum concentrations and AUC for Fc-OB protein are consistent with lower clearance. Fc-OB protein will yield substantially higher systemic exposure when compared to OB protein. Results are shown in Table 4 below:

TABLE 4

Pharmacokinetic Properties

| | Species | | | | | |
|---|---|---|---|---|---|---|
| | CD-1 Mice | | CD-1 Mice | | Beagle Dogs | |
| | Route of Administration | | | | | |
| | Intravenous | | Subcutaneous | | Subcutaneous | |
| | OB protein | Fc-OB protein | OB protein | Fc-OB protein | OB protein | Fc-OB protein |
| Dose Level (mg/kg) | 1 | 1 | 1 | 1 | 0.5 | 0.5 |
| Peak Time (h) | | | 0.14 | 6 | 2.8 | 8 |
| Peak Serum Concentration (ng/mL) | | | 1520 | 7550 | 300 | 1120 |
| AUC (ng · h/mL) | 1470 | 366000 | 1230 | 132000 | 2200 | 52500 |
| Half-life (h) | 0.491 | 21.4 | 0.388 | | 2.13 | 22.9 |
| Clearance (mL/h/kg) | 681 | 2.73 | | | | |

EXAMPLE 5

This example demonstrates that in normal mice which are not obese and do not have elevated blood lipid levels, administration of human recombinant Fc-OB protein results in a lowering of cholesterol, glucose and triglyceride levels. In addition, this example demonstrates that these levels remain low over a three day recovery period.

Normal CD1 mice were administered recombinant human Fc-OB protein via subcutaneous injections. Blood samples were taken 24 hours after day 23, the last day of injection. As discussed above, the animals lost weight at the dosages administered. As shown in Table 5, the mice had substantial reduction of serum cholesterol, glucose and triglycerides in a dose-dependent fashion when compared to controls:

TABLE 5

| Dose | Glucose | Cholesterol | Triglycerides |
| --- | --- | --- | --- |
| PBS | 232.6 +/− 15.1 | 67.8 +/− 3.6 | 52.6 +/− 3.7 |
| 1 mg/kg/day | 225.8 +/− 29.1 | 54 +/− 5.6 | 43 +/− 8.7 |
| 10 mg/kg/day | 193.2 +/− 21.4 | 53.4 +/− 5.7 | 38 +/− 11 |
| 1 mg/kg every 2 days | 242.0 +/− 9.3 | 52.6 +/− 4.4 | 40.8 +/− 7.2 |
| 10 mg/kg every 2 days | 197.4 +/− 27.9 | 51.4 +/− 5.9 | 29.8 +/− 6.3 |
| 1 mg/kg every 3 days | 244.8 +/− 19.5 | 60.8 +/− 7.3 | 54 +/− 7.1 |
| 10 mg/kg every 3 days | 188 +/− 31.2 | 52.2 +/− 6.9 | 26.2 +/− 10.7 |

These data demonstrate that the Fc-OB protein, or analogs or derivatives thereof, are effective blood lipid lowering agents.

EXAMPLE 6

A obese human patient is administered human Fc-OB protein, or analog or derivative for the purpose of weight reduction. The obese patient also has elevated levels of blood lipids, including elevated levels of cholesterol, above 200 mg/100 ml. The patient attains a satisfactory weight reduction over the course of Fc-OB therapy. A maintenance dose of Fc-OB protein or analog or derivative is administered to the non-obese patient to maintain lowered blood lipid levels, including lowered cholesterol levels, below 200 mg/100 ml. The dose administered is insufficient to result in further weight loss. Administration is chronic. Levels of circulating Fc-OB protein or analog or derivative may be monitored using a diagnostic kit, such as an antibody assay against the OB protein (or other antigenic source if applicable).

EXAMPLE 7

A non-obese human patient undergoes coronary bypass surgery or other invasive treatment to alleviate advanced stages arterial plaque formation. After the surgery, the patient is administered a maintenance dose of Fc-OB protein or analog or derivative in order to prevent the re-formation of arterial plaque. The dose administered is insufficient to result in weight loss. Administration is chronic. Levels of circulating Fc-OB protein or analog or derivative may be monitored using a diagnostic kit, such as an antibody assay against the OB protein (or other antigenic source if applicable).

EXAMPLE 8

A non-obese human patient experiences hypertension due to restricted blood flow from clogged arteries. The patient is administered a dose of Fc-OB protein, or analog or derivative thereof sufficient to reduce arterial plaque resulting in clogged arteries. Thereafter, the patient is monitored for further arterial plaque formation, and hypertension. If the condition re-appears, the patient is re-administered an effective amount of Fc-OB protein, analog or derivative sufficient to restore blood flow, yet insufficient to result in weight loss. Levels of circulating Fc-OB protein or analog or derivative may be monitored using a diagnostic kit, such as an antibody assay against the Fc-OB protein (or other antigenic source if applicable).

EXAMPLE 9

A human patient experiences gall stones. Either the gall stones are not removed and the formation of additional gall stones is sought to be avoided, or the gall stones are removed but the gall bladder remains (as, for example, using laser or ultrasonic surgery) and the formation of additional gall stones is sought to be avoided. The patient is administered an effective amount of Fc-OB protein, analog or derivative thereof to result in prevention of accumulation of additional gall stones or re-accumulation of gall stones. Levels of circulating Fc-OB protein or analog or derivative may be monitored using a diagnostic kit, such as an antibody assay against the Fc-OB protein (or other antigenic source if applicable).

EXAMPLE 10

A diabetic human patient desires to use decreased dosages of insulin for treatment of diabetes. The patient is administered an effective amount of Fc-OB protein, analog or derivative thereof to result in an increase in lean tissue mass. The patient's sensitivity to insulin increases, and the dosage of insulin necessary to alleviate symptoms of diabetes is decreased, either in terms of a decrease in the units of insulin needed, or in terms of a decrease in the number of injections of insulin needed per day. Levels of circulating Fc-OB protein or analog or derivative may be monitored using a diagnostic kit, such as an antibody assay against the OB protein (or other antigenic source if applicable).

EXAMPLE 11

A non-obese human patient desires an increase in lean tissue mass for therapeutic purposes, such as recovery from illness which depleted lean tissue mass. The patient is administered an effective amount of Fc-OB protein, analog or derivative thereof to result in the desired increase in lean tissue mass. Increase in lean tissue mass is monitored using DEXA scanning. Levels of circulating Fc-OB protein or analog or derivative may be monitored using a diagnostic kit, such as an antibody assay against the OB protein (or other antigenic source if applicable).

Materials and Methods

Animals. Wild type CD1 mice and (+/+) C57B16 mice were used for the above examples. The age of the mice at the initial time point was 8 weeks, and the animals were weight stabilized.

Feeding and Weight Measurement. Mice were given ground rodent chow (PMI Feeds, Inc.) in powdered food feeders (Allentown Caging and Equipment) which allowed a more accurate and sensitive measurement than use of regular block chow. Weight was measured at the same time each day (2:00 p.m.), for the desired period. Body weight on the day prior to the injection was defined as baseline weight. The mice used weighed 18-22 grams.

Housing. Mice were single-housed, and maintained under humane conditions.

Administration of Protein or Vehicle. Protein (as described below) or vehicle (phosphate buffered saline, pH 7.4) were administered by subcutaneous injections or intravenously.

Controls. Control animals were those who were injected with the vehicle alone without either Fc-OB fusion protein or OB protein added to the vehicle.

Protein. Sequence ID. Nos. 1, 2 and 3 set forth murine recombinant OB DNA and protein (FIG. 1), and Sequence ID. Nos. 4, 5 and 6 set forth an analog recombinant human OB DNA and protein (FIG. 2). As noted above recombinant human OB protein as in SEQ. ID. NO. 6 has a lysine residue at position 35 and an isoleucine residue at position 74. Furthermore, the recombinant human protein set forth in Zhang et al., Nature, supra, and PCT publication WO 96/05309 (Dec. 22, 1996) (both incorporated by reference including figures), and the murine and human analog recombinant proteins of FIGS. 1 and 2 are illustrative of the OB protein which may be used in forming the Fc-OB fusion protein of the present methods of treatment and manufacture of a medicament. Other OB or Fc proteins or analogs or derivatives thereof may also be used to form the Fc-OB fusion protein.

Herein, the first amino acid of the amino acid sequence for recombinant OB protein is referred to as +1, and is valine, and the amino acid at position −1 is methionine. The C-terminal amino acid is number 146 (cysteine) (see FIGS. 1 and 2). The first amino acid sequence for recombinant human Fc-OB protein of FIG. 3 is referred to as +1, and is glutamate, and the amino acid at position −1 is methionine. The C-terminal amino acid is number 378 (cysteine). The first amino acid sequence for the recombinant human Fc-OB protein variant of FIG. 4 is referred to as +1, and is glutamate, and the amino acid at position −1 is methionine. The C-terminal amino acid is number 378 (cysteine). The first amino acid sequence for the recombinant human Fc-OB protein variant of FIG. 5 is referred to as +1, and is aspartic acid, and the amino acid at position −1 is methionine. The C-terminal amino acid is number 373 (cysteine). The first amino acid sequence for the recombinant human Fc-OB protein variant of FIG. 6 is referred to as +1, and is aspartic acid, and the amino acid at position −1 is methionine. The C-terminal amino acid is number is 373 (cysteine).

Expression Vector and Host Strain.

The plasmid expression vector used is pAMG21 (ATCC accession number 98113), which is a derivative of pCFM1656 (ATCC accession number 69576) and contains appropriate restriction sites for insertion of genes downstream from the lux.PR promoter (see U.S. Pat. No. 5,169,318 for a description of the lux expression system). The Fc-OB DNA, described below and shown in FIGS. 3-6, was created and ligated into the expression vector pAMG21 linearized with restriction endonucleases NdeI and BamHI and transformed into the *E. coli* host strain, FM5. *E. coli* FM5 cells were derived at Amgen Inc., Thousand Oaks, Calif. from *E. coli* K-12 strain (Bachmann, et al., Bacterial. Rev. 40: 116-167 (1976)) and contain the integrated lambda phage repressor gene, $cI_{857}$ (Sussman et al., C. R. Acad. Sci. 254: 1517-1579 (1962)). Vector production, cell transformation, and colony selection were performed by standard methods, (e.g., Sambrook, et al., Molecular Cloning: A Laboratory Manual, 2d Edition, Cold Spring Harbor Laboratory Press, Cold Spring Harbor, N.Y.) Host cells were grown in LB media.

Fc-OB DNA Construction

The plasmid pFc-A3 (described below) served as the source of sequence for human immunoglobulin IgG-1 heavy chain from amino acid number 99 (Glu) to the natural carboxyl terminus. The human IgG-1 sequence can be obtained from Genebank (P01857).

The human OB sequence is disclosed above as well as Zhang et al., Nature, supra, and PCT publication WO 96/05309 both incorporated by reference including drawings. The OB DNA was ligated into the expression vector pCFM1656 linearized with restriction endonucleases XbaI and BamHI using standard cloning procedures, e.g., Sambrook, et al., Molecular Cloning: A Laboratory Manual, 2d Edition, Cold Spring Harbor Laboratory Press, Cold Spting Harbor, N.Y. The plasmid pCFM1656 carrying the OB DNA sequence served as the source of sequence for the recombinant human OB gene.

The genetic fusing of these two sequences was carried out by the method of PCR overlap extension (Ho, S. N., et al., *Site Directed Mutagenesis By Overlap Extension Using The Polymerase Chain Reaction*, Gene 77:51-59(1989)). The product of the PCR was cleaved with restriction endonuclease NdeI to create a 5'-cohesive end and with restriction endonuclease BamHI to create a 3'-cohesive terminus. The vector, pAMG21, was similarly cleaved. A ligation was performed with the fusion fragment and the linearized vector. Ligated DNA was transformed by electroporation into the *E. coli* host strain. Clones surviving on kanamycin (50 μg/ml) selection agar plates were checked for expression of Fc-OB-sized protein. Plasmid from individual clones was isolated and the sequence of the gene coding region verified.

When additional modifications of the Fc-OB gene were desired, the PCR technique was used again to engineer the changes. Two sets of changes were performed at the N-terminus of the Fc portion of the fusion protein (SEQ. ID. No. 9) to create the variants SEQ. ID. NOS. 12 and 15. Another variant was constructed to introduce four amino acid substitutions to ablate the Fc-receptor binding site (leucine at position 15 substituted with glutamate), and the complement (C1q) binding site (glutamate at position 98 substituted with alanine, lysine at position 100 substituted with alanine, and lysine at position 102 substituted with alanine (See, Xin Xiao Zheng et. al, J. Immunol. 154: 5590-5600 (1995)). The template for this construct was Seq. ID. No. 15 and the resulting variant was SEQ. ID. Nos. 18.

pFC-A3 Vector Construction

A plasmid, pFc-A3, containing the region encoding the Fc portion of human immunoglobulin IgG-1 heavy chain (See Ellison, J. W. et. al, Nucleic Acids Res. 10:4071-4079 (1982)), from the first amino acid. Glu-99 of the hinge domain to the carboxyl terminus plus a 5'-NotI fusion site and 3'-SalI and XbaI sites, was made by PCR amplification of the human spleen cDNA library. PCR reactions were in a final volume of 100 ml and employed 2 units of Vent DNA polymerase in 20 mM Tris-HCl (pH 8.8), 10 mM KCl, 10 mM $(NH_4)_2SO_4$, 2 mM $MgSO_4$, 0.1% Triton X-100 with 400 mM each dNTP and 1 ng of the cDNA library to be amplified together with 1 uM of each primer. Reactions were initiated by denaturation at 95° C. for 2 min, followed by 30 cycles of 95° C. for 30 s, 55° C. for 30 s, and 73° C. for 2 min. The 5'-primer incorporated a NotI site immediately 5' to the first residue (Glu-99) of the hinge domain of IgG-1. The 3'-primer incorporated SalI and XbaI sites. The 717 base pair PCR product was digested with NotI and SalI, the resulting DNA fragment was isolated by electrophoresis through 1% agarose and purified and cloned into NotI, SalI-digested pBluescript II KS vector (Stratagene). The insert in the resulting plasmid, pFc-A3, was sequenced to confirm the fidelity of the PCR reaction.

Methods for Production

The methods below for production have been used to produce biologically active recombinant methionyl murine or human analog OB protein and Fc-OB fusion proteins. Similar methods may be used to prepare biologically active methionyl human OB protein.

Fermentation Process

A batch fermentation process was used. Media compositions are set forth below.

A portion of the media consisting of primarily nitrogen sources was sterilized (by raising temperature to 120-123° C. for 25-35 minutes) in the fermentation vessel. Upon cooling, carbon, magnesium, phosphate, and trace metal sources were added aseptically. An overnight culture of the above recombinant murine protein-producing bacteria of 500 mL (grown in LB broth) was added to the fermentor. When the culture optical density (measured at 600 nm as an indicator for cell density) reached 15-25 absorption units, an autoinducer solution (0.5 mg/mL homoserine lactone) was added (1 mL/L) to the culture to induce the recombinant gene expression. The fermentation process was allowed to continue for additional 10 to 16 hours, followed by harvesting the broth by centrifugation.

Media Composition:

| Batch: | 34 g/L | Yeast extract |
|---|---|---|
| | 78 g/L | Soy peptone |
| | 0.9 g/L | Potassium chloride |
| | 5.0 g/L | Hexaphos |
| | 1.7 g/L | Citric acid |
| | 120 g/L | Glycerol |
| | 0.5 g/L | $MgSO_4.7H_2O$ |
| | 0.2 mL/L | Trace Metal Solution |
| | 0.5 mL/L | P2000 Antifoam |

Trace Metal Solution:
  Ferric Chloride ($FeCl_3.6H_2O$): 27 g/L
  Zinc Chloride ($ZnCl_2.4H_2O$): 2 g/L
  Cobalt Chloride ($CoCl_2.6H_2O$): 2 g/L
  Sodium Molybdate ($NaMoO_4.2H_2O$): 2 g/L
  Calcium Chloride ($CaCl_2.2H_2O$): 1 g/L
  Cupric Sulfate ($CuSO_4.5H_2O$): 1.9 g/L
  Boric Acid ($H_3BO_3$): 0.5 g/L
  Manganese Chloride ($MnCl_2.4H_2O$): 1.6 g/L
  Sodium Citrate dihydrate: 73.5 g/L Purification Process for Human Fc-OB Fusion Protein Purification for human Fc-OB fusion protein was accomplished by the steps below (unless otherwise noted, the following steps were performed at 4° C.). Purification for murine and human OB protein is disclosed in PCT publication WO 96/05309, supra, herein incorporated by reference.

1. Cell paste. *E. coli* cell paste was suspended in 5 times volumes of distilled water. The cells in the water were further broken by two passes through a microfluidizer. The broken cells were centrifuged at 4.2 k rpm for 1 hour in a Beckman JB-6 centrifuge with a J5-4.2 rotor.

2. Inclusion body wash. The supernatant from above was removed and the pellet was resuspended with five volumes of distilled water. The mixture was centrifuged as in step 1.

3. Solubilization. The pellet was solubilized with 10 volumes of 50 mM tris, pH 8.5, 8 M guanidine hydrochloride, 10 mM dithiothreitol and stirred for one hour at room temperature. The solution is made 40 mM cystamine dihydrochloride and stirred for one hour.

4. The solution from step 3 is added to 20 to 30 volumes of the following refold solution: 50 mM tris, pH 8.5, 0.8 M arginine, 2 M urea, and 4 mM cysteine. The refold is stirred for 16 hours at 8° C.

5. Buffer exchange. The solution from step 4 is concentrated and diafiltered into 10 mM tris, pH 8.5.

6. Acid precipitation. The solution from step 5 is adjusted to pH 4.75 with 50% glacial acid and incubated for 30 minutes at room temperature. The solution is filtered.

7. Cation exchange chromatography. The solution from step 6 is adjusted to pH 7.0 and loaded onto a CM Sepharose Fast Flow column at 10° C. A twenty column volume gradient is done at 10 mM phosphate, pH 7.0, 0 to 0.1 M NaCl.

8. Anion exchange chromatography. The CM elution pool from step 7 is diluted 5 fold with 5 mM tris, pH 7.5 and loaded onto a Q Sepharose Fast Flow at 10° C. A 20 column volume gradient is done at 10 mM tris, pH 7.5, 0 to 0.2M NaCl.

9. Hydrophobic interaction chromatography. The Q sepharose pool is made 0.75M ammonium sulfate and loaded on a methyl Macroprep hydrophobic interaction column at room temperature. A 20 column volume gradient is done at 10 mM phosphate, pH 7.0, 0.75M to 0M ammonium sulfate.

10. Buffer exchange. The pool from step 9 is concentrated as necessary and dialyzed against PBS buffer.

While the present invention has been described in terms of preferred embodiments, it is understood that variations and modifications will occur to those skilled in the art. Therefore, it is intended that the appended claims cover all such equivalent variations which come within the scope of the invention as claimed.

SEQUENCE LISTING

<160> NUMBER OF SEQ ID NOS: 23

<210> SEQ ID NO 1
<211> LENGTH: 491
<212> TYPE: DNA
<213> ORGANISM: mouse

<400> SEQUENCE: 1

```
tctagatttg agtttaact tttagaagga ggaataacat atggtaccga tccagaaagt      60
tcaggacgac accaaaacct taattaaaac gatcgttacg cgtatcaacg acatcagtca    120
cacccagtcg gtctccgcta aacagcgtgt taccggtctg gacttcatcc cgggtctgca    180
cccgatccta agcttgtcca aaatggacca gaccctggct gtataccagc aggtgttaac    240
ctccctgccg tcccagaacg ttcttcagat cgctaacgac ctcgagaacc ttcgcgacct    300
```

```
gctgcacctg ctggcattct ccaaatcctg ctccctgccg cagacctcag gtcttcagaa    360
accggaatcc ctggacgggg tcctggaagc atccctgtac agcaccgaag ttgttgctct    420
gtcccgtctg cagggttccc ttcaggacat ccttcagcag ctggacgttt ctccggaatg    480
ttaatggatc c                                                         491

<210> SEQ ID NO 2
<211> LENGTH: 491
<212> TYPE: DNA
<213> ORGANISM: mouse

<400> SEQUENCE: 2
agatctaaac tcaaaattga aaatcttcct ccttattgta taccatggct aggtctttca     60
agtcctgctg tggttttgga attaattttg ctagcaatgc gcatagttgc tgtagtcagt    120
gtgggtcagc cagaggcgat tgtcgcaca atggccagac tgaagtagg gcccagacgt      180 gggctaggat tcgaacaggt tttacctggt ctgggaccga catatggtcg tccacaattg    240
gagggacggc agggtcttgc aagaagtcta gcgattgctg gagctcttgg aagcgctgga    300
cgacgtggac gaccgtaaga ggtttaggac gagggacggc gtctggagtc cagaagtctt    360
tggccttagg gacctgcccc aggaccttcg tagggacatg tcgtggcttc aacaacgaga    420
cagggcagac gtcccaaggg aagtcctgta ggaagtcgtc gacctgcaaa gaggccttac    480
aattacctag g                                                         491

<210> SEQ ID NO 3
<211> LENGTH: 147
<212> TYPE: PRT
<213> ORGANISM: mouse

<400> SEQUENCE: 3

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ala Lys Gln Arg Val Thr Gly Leu Asp Phe Ile Pro Gly Leu His Pro
            35                  40                  45

Ile Leu Ser Leu Ser Lys Met Asp Gln Thr Leu Ala Val Tyr Gln Gln
        50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145

<210> SEQ ID NO 4
<211> LENGTH: 454
<212> TYPE: DNA
<213> ORGANISM: Artificial
<220> FEATURE:
<223> OTHER INFORMATION: human metOB analog 1; 5' to 3' cDNA
```

-continued

```
<400> SEQUENCE: 4
catatggtac cgatccagaa agttcaggac gacaccaaaa ccttaattaa aacgatcgtt      60
acgcgtatca acgacatcag tcacacccag tcggtgagct ctaaacagcg tgttacaggc     120
ctggacttca tcccgggtct gcacccgatc ctgaccttgt ccaaaatgga ccagaccctg     180
gctgtatacc agcagatctt aacctccatg ccgtcccgta acgttcttca gatctctaac     240
gacctcgaga accttcgcga cctgctgcac gtgctggcat tctccaaatc ctgccacctg     300
ccatgggctt caggtcttga ctctggac tctctgggcg gggtcctgga agcatccggt       360
tacagcaccg aagttgttgc tctgtcccgt ctgcagggtt cccttcagga catgctttgg     420
cagctggacc tgtctccggg ttgttaatgg atcc                                 454

<210> SEQ ID NO 5
<211> LENGTH: 454
<212> TYPE: DNA
<213> ORGANISM: Artificial
<220> FEATURE:
<223> OTHER INFORMATION: human metOB analog 1; 3' to 5' cDNA

<400> SEQUENCE: 5
gtataccatg gctaggtctt tcaagtcctg ctgtggtttt ggaattaatt ttgctagcaa      60
tgcgcatagt tgctgtagtc agtgtgggtc agccactcga gatttgtcgc acaatgtccg     120
gacctgaagt agggcccaga cgtgggctag gactggaaca ggttttacct ggtctgggac     180
cgacatatgg tcgtctagaa ttggaggtac ggcagggcat tgcaagaagt ctagagattg     240
ctggagctct tggaagcgct ggacgacgtg cacgaccgta agaggtttag gacggtggac     300
ggtacccgaa gtccagaact ctgagacctg agagacccgc cccaggacct tcgtaggcca     360
atgtcgtggc ttcaacaacg agacagggca gacgtcccaa gggaagtcct gtacgaaacc     420
gtcgacctgg acagaggccc aacaattacc tagg                                 454

<210> SEQ ID NO 6
<211> LENGTH: 147
<212> TYPE: PRT
<213> ORGANISM: Artificial
<220> FEATURE:
<223> OTHER INFORMATION: human metOB analog 1

<400> SEQUENCE: 6

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Arg Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Leu Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140
```

Pro Gly Cys
145

<210> SEQ ID NO 7
<211> LENGTH: 1150
<212> TYPE: DNA
<213> ORGANISM: Artificial
<220> FEATURE:
<223> OTHER INFORMATION: human metFc-OB protein analog 1; 5' to 3' cDNA

<400> SEQUENCE: 7

| | | |
|---|---|---|
| catatggaac ccaaatcttg tgacaaaact cacacatgcc caccgtgccc agcacctgaa | 60 |
| ctcctggggg gaccgtcagt cttcctcttc cccccaaaac ccaaggacac cctcatgatc | 120 |
| tcccggaccc ctgaggtcac atgcgtggtg gtggacgtga gccacgaaga ccctgaggtc | 180 |
| aagttcaact ggtacgtgga cggcgtggag gtgcataatg ccaagacaaa gccgcgggag | 240 |
| gagcagtaca acagcacgta ccgtgtggtc agcgtcctca ccgtcctgca ccaggactgg | 300 |
| ctgaatggca aggagtacaa gtgcaaggtc tccaacaaag ccctcccagc ccccatcgag | 360 |
| aaaaccatct ccaaagccaa agggcagccc cgagaaccac aggtgtacac cctgcccca | 420 |
| tcccgggatg agctgaccaa gaaccaggtc agcctgacct gcctggtcaa aggcttctat | 480 |
| cccagcgaca tcgccgtgga gtgggagagc aatgggcagc cggagaacaa ctacaagacc | 540 |
| acgcctcccg tgctggactc cgacggctcc ttcttcctct acagcaagct caccgtggac | 600 |
| aagagcaggt ggcagcaggg gaacgtcttc tcatgctccg tgatgcatga ggctctgcac | 660 |
| aaccactaca cgcagaagag cctctccctg tctccgggta aagtaccgat ccagaaagtt | 720 |
| caggacgaca ccaaaacctt aattaaaacg atcgttacgc gtatcaacga catcagtcac | 780 |
| acccagtcgg tgagctctaa acagaaagtt acaggcctgg acttcatccc gggtctgcac | 840 |
| ccgatcctga ccttgtccaa aatggaccag accctggctg tataccagca gatcttaacc | 900 |
| tccatgccgt cccgtaacgt tatccagatc tctaacgacc tcgagaacct cgcgacctg | 960 |
| ctgcacgtgc tggcattctc caaatcctgc cacctgccat gggcttcagg tcttgagact | 1020 |
| ctggactctc tgggcggggt cctggaagca tccggttaca gcaccgaagt tgttgctctg | 1080 |
| tcccgtctgc agggttccct tcaggacatg cttttggcag ctggacctgtc tccgggttgt | 1140 |
| taatggatcc | 1150 |

<210> SEQ ID NO 8
<211> LENGTH: 1150
<212> TYPE: DNA
<213> ORGANISM: Artificial
<220> FEATURE:
<223> OTHER INFORMATION: human metFc-OB protein analog 1; 3' to 5' cDNA

<400> SEQUENCE: 8

| | | |
|---|---|---|
| gtataccttg ggtttagaac actgttttga gtgtgtacgg gtggcacggg tcgtggactt | 60 |
| gaggaccccc ctggcagtca gaaggagaag gggggttttg ggttcctgtg ggagtactag | 120 |
| agggcctggg gactccagtg tacgcaccac cacctgcact cggtgcttct gggactccag | 180 |
| ttcaagttga ccatgcacct gccgcacctc cacgtattac ggttctgttt cggcgccctc | 240 |
| ctcgtcatgt tgtcgtgcat ggcacaccag tcgcaggagt ggcaggacgt ggtcctgacc | 300 |
| gacttaccgt tcctcatgtt cacgttccag aggttgtttc gggagggtcg ggggtagctc | 360 |
| ttttggtaga ggtttcggtt tcccgtcggg gctcttggtg tccacatgtg gacggggagt | 420 |
| agggccctac tcgactggtt cttggtccag tcggactgga cggaccagtt tccgaagata | 480 |

-continued

```
gggtcgctgt agcggcacct caccctctcg ttacccgtcg gcctcttgtt gatgttctgg    540
tgcggagggc acgacctgag gctgccgagg aagaaggaga tgtcgttcga gtggcacctg    600
ttctcgtcca ccgtcgtccc cttgcagaag agtacgaggc actacgtact ccgagacgtg    660
ttggtgatgt gcgtcttctc ggagagggac agaggcccat tcatggcta ggtctttcaa    720 gtcctgctgt ggttttggaa ttaattttgc tagcaatgcg catagttgct gtagtcagtg    780
tgggtcagcc actcgagatt tgtctttcaa tgtccggacc tgaagtaggg cccagacgtg    840
ggctaggact ggaacaggtt ttacctggtc tgggaccgac atatggtcgt ctagaattgg    900
aggtacggca gggcattgca ataggtctag agattgctgg agctcttgga agcgctggac    960
gacgtgcacg accgtaagag gtttaggacg gtggacggta cccgaagtcc agaactctga   1020
gacctgagag acccgcccca ggaccttcgt aggccaatgt cgtggcttca acaacgagac   1080
agggcagacg tcccaaggga agtcctgtac gaaaccgtcg acctggacag aggcccaaca   1140
attacctagg                                                          1150
```

<210> SEQ ID NO 9
<211> LENGTH: 379
<212> TYPE: PRT
<213> ORGANISM: Artificial
<220> FEATURE:
<223> OTHER INFORMATION: human metFc-OB protein analog 1

<400> SEQUENCE: 9

```
Met Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Val Pro Ile Gln Lys Val Gln
225                 230                 235                 240

Asp Asp Thr Lys Thr Leu Ile Lys Thr Ile Val Thr Arg Ile Asn Asp
```

```
                     245                 250                 255
Ile Ser His Thr Gln Ser Val Ser Ser Lys Gln Lys Val Thr Gly Leu
                260                 265                 270

Asp Phe Ile Pro Gly Leu His Pro Ile Leu Thr Leu Ser Lys Met Asp
            275                 280                 285

Gln Thr Leu Ala Val Tyr Gln Gln Ile Leu Thr Ser Met Pro Ser Arg
        290                 295                 300

Asn Val Ile Gln Ile Ser Asn Asp Leu Glu Asn Leu Arg Asp Leu Leu
305                 310                 315                 320

His Val Leu Ala Phe Ser Lys Ser Cys His Leu Pro Trp Ala Ser Gly
                325                 330                 335

Leu Glu Thr Leu Asp Ser Leu Gly Gly Val Leu Glu Ala Ser Gly Tyr
            340                 345                 350

Ser Thr Glu Val Val Ala Leu Ser Arg Leu Gln Gly Ser Leu Gln Asp
        355                 360                 365

Met Leu Trp Gln Leu Asp Leu Ser Pro Gly Cys
    370                 375

<210> SEQ ID NO 10
<211> LENGTH: 1150
<212> TYPE: DNA
<213> ORGANISM: Artificial
<220> FEATURE:
<223> OTHER INFORMATION: human metFc-OB protein analog 2; 5' to 3' cDNA

<400> SEQUENCE: 10
catatggaac caaatctgc tgacaaaact cacacatgtc caccttgtcc agctccggaa      60
ctcctggggg gtccttcagt cttcctcttc cccccaaaac ccaaggacac cctcatgatc     120
tcccggaccc ctgaggtcac atgcgtggtg gtggacgtga gccacgaaga ccctgaggtc     180
aagttcaact ggtacgtgga cggcgtggag gtgcataatg ccaagacaaa gccgcgggag     240
gagcagtaca acagcacgta ccgtgtggtc agcgtcctca ccgtcctgca ccaggactgg     300
ctgaatggca aggagtacaa gtgcaaggtc tccaacaaag ccctcccagc ccccatcgag     360
aaaaccatct ccaaagccaa agggcagccc cgagaaccac aggtgtacac cctgccccca     420
tcccgggatg agctgaccaa gaaccaggtc agcctgacct gcctggtcaa aggcttctat     480
cccagcgaca tcgccgtgga gtgggagagc aatgggcagc cggagaacaa ctacaagacc     540
acgcctcccg tgctggactc cgacggctcc ttcttcctct acagcaagct caccgtggac     600
aagagcaggt ggcagcaggg gaacgtcttc tcatgctccg tgatgcatga ggctctgcac     660
aaccactaca cgcagaagag cctctccctg tctccgggta agtaccgatc cagaaagtt     720
caggacgaca ccaaaacctt aattaaaacg atcgttacgc gtatcaacga catcagtcac     780
acccagtcgg tgagctctaa acagaaagtt acaggcctgg acttcatccc gggtctgcac     840
ccgatcctga ccttgtccaa aatggaccag accctggctg tataccagca gatcttaacc     900
tccatgccgt cccgtaacgt tatccagatc tctaacgacc tcgagaacct tcgcgacctg     960
ctgcacgtgc tggcattctc caaatcctgc cacctgccat gggcttcagg tcttgagact    1020
ctggactctc tgggcggggt cctggaagca tccggttaca gcaccgaagt tgttgctctg    1080
tcccgtctgc agggttccct tcaggacatg ctttggcagc tggacctgtc tccgggttgt    1140
taatggatcc                                                           1150

<210> SEQ ID NO 11
<211> LENGTH: 1150
<212> TYPE: DNA
```

<213> ORGANISM: Artificial
<220> FEATURE:
<223> OTHER INFORMATION: human metFc-OB protein analog 2; 3' to 5'

<400> SEQUENCE: 11

```
gtataccttg gttttagacg actgttttga gtgtgtacag gtggaacagg tcgaggcctt      60
gaggacccccc caggaagtca gaaggagaag gggggttttg ggttcctgtg ggagtactag    120
agggcctggg gactccagtg tacgcaccac cacctgcact cggtgcttct gggactccag    180
ttcaagttga ccatgcacct gccgcacctc cacgtattac ggttctgttt cggcgccctc    240
ctcgtcatgt tgtcgtgcat ggcacaccag tcgcaggagt ggcaggacgt ggtcctgacc    300
gacttaccgt tcctcatgtt cacgttccag aggttgtttc gggagggtcg ggggtagctc    360
ttttggtaga ggtttcggtt tcccgtcggg gctcttggtg tccacatgtg gacgggggt      420
agggccctac tcgactggtt cttggtccag tcggactgga cggaccagtt tccgaagata    480
gggtcgctgt agcggcacct cacccctctcg ttacccgtcg gcctcttgtt gatgttctgg    540
tgcggagggc acgacctgag gctgccgagg aagaaggaga tgtcgttcga gtggcacctg    600
ttctcgtcca ccgtcgtccc cttgcagaag agtacgaggc actacgtact ccgagacgtg    660
ttggtgatgt gcgtcttctc ggagagggac agaggcccat ttcatggcta ggtctttcaa    720
gtcctgctgt ggttttggaa ttaattttgc tagcaatgcg catagttgct gtagtcagtg    780
tgggtcagcc actcgagatt tgtctttcaa tgtccggacc tgaagtaggg cccagacgtg    840
ggctaggact ggaacaggtt ttacctggtc tgggaccgac atatggtcgt ctagaattgg    900
aggtacggca gggcattgca ataggtctag agattgctgg agctcttgga agcgctggac    960
gacgtgcacg accgtaagag gtttaggacg gtggacggta cccgaagtcc agaactctga   1020
gacctgagag acccgcccca ggaccttcgt aggccaatgt cgtggcttca acaacgagac   1080
agggcagacg tcccaaggga agtcctgtac gaaaccgtcg acctggacag aggcccaaca   1140
attacctagg                                                          1150
```

<210> SEQ ID NO 12
<211> LENGTH: 379
<212> TYPE: PRT
<213> ORGANISM: Artificial
<220> FEATURE:
<223> OTHER INFORMATION: human metFc-OB protein analog 2

<400> SEQUENCE: 12

```
Met Glu Pro Lys Ser Ala Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125
```

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Val Pro Ile Gln Lys Val Gln
225                 230                 235                 240

Asp Asp Thr Lys Thr Leu Ile Lys Thr Ile Val Thr Arg Ile Asn Asp
                245                 250                 255

Ile Ser His Thr Gln Ser Val Ser Ser Lys Gln Lys Val Thr Gly Leu
                260                 265                 270

Asp Phe Ile Pro Gly Leu His Pro Ile Leu Thr Leu Ser Lys Met Asp
            275                 280                 285

Gln Thr Leu Ala Val Tyr Gln Gln Ile Leu Thr Ser Met Pro Ser Arg
290                 295                 300

Asn Val Ile Gln Ile Ser Asn Asp Leu Glu Asn Leu Arg Asp Leu Leu
305                 310                 315                 320

His Val Leu Ala Phe Ser Lys Ser Cys His Leu Pro Trp Ala Ser Gly
                325                 330                 335

Leu Glu Thr Leu Asp Ser Leu Gly Gly Val Leu Glu Ala Ser Gly Tyr
            340                 345                 350

Ser Thr Glu Val Val Ala Leu Ser Arg Leu Gln Gly Ser Leu Gln Asp
        355                 360                 365

Met Leu Trp Gln Leu Asp Leu Ser Pro Gly Cys
370                 375

<210> SEQ ID NO 13
<211> LENGTH: 1135
<212> TYPE: DNA
<213> ORGANISM: Artificial
<220> FEATURE:
<223> OTHER INFORMATION: human metFc-OB protein analog 3; 5' to 3'

<400> SEQUENCE: 13
catatggaca aaactcacac atgtccacct tgtccagctc cggaactcct ggggggtcct      60
tcagtcttcc tcttcccccc aaaacccaag gacaccctca tgatctcccg gacccctgag     120
gtcacatgcg tggtggtgga cgtgagccac gaagaccctg aggtcaagtt caactggtac     180
gtggacggcg tggaggtgca taatgccaag acaaagccgc gggaggagca gtacaacagc     240
acgtaccgtg tggtcagcgt cctcaccgtc ctgcaccagg actggctgaa tggcaaggag     300
tacaagtgca aggtctccaa caaagccctc ccagccccca tcgagaaaac catctccaaa     360
gccaaagggc agccccgaga accacaggtg tacaccctgc ccccatcccg ggatgagctg     420
accaagaacc aggtcagcct gacctgcctg gtcaaaggct tctatcccag cgacatcgcc     480
gtggagtggg agagcaatgg gcagccggag aacaactaca agaccacgcc tcccgtgctg     540
gactccgacg gctccttctt cctctacagc aagctcaccg tggacaagag caggtggcag     600
caggggaacg tcttctcatg ctccgtgatg catgaggctc tgcacaacca ctacacgcag     660

```
aagagcctct ccctgtctcc gggtaaagta ccgatccaga aagttcagga cgacaccaaa    720
accttaatta aaacgatcgt tacgcgtatc aacgacatca gtcacaccca gtcggtgagc    780
tctaaacaga aagttacagg cctggacttc atcccgggtc tgcacccgat cctgaccttg    840
tccaaaatgg accagaccct ggctgtatac cagcagatct taacctccat gccgtcccgt    900
aacgttatcc agatctctaa cgacctcgag aaccttcgcg acctgctgca cgtgctggca    960
ttctccaaat cctgccacct gccatgggct tcaggtcttg agactctgga ctctctgggc   1020
ggggtcctgg aagcatccgg ttacagcacc gaagttgttg ctctgtcccg tctgcagggt   1080
tcccttcagg acatgctttg gcagctggac ctgtctccgg ttgttaatg gatcc        1135

<210> SEQ ID NO 14
<211> LENGTH: 1135
<212> TYPE: DNA
<213> ORGANISM: Artificial
<220> FEATURE:
<223> OTHER INFORMATION: human metFc-OB protein analog 3; 3' to 5'

<400> SEQUENCE: 14
gtatacctgt tttgagtgtg tacaggtgga acaggtcgag gccttgagga ccccccagga     60
agtcagaagg agaagggggg ttttgggttc ctgtgggagt actagagggc ctggggactc    120
cagtgtacgc accaccacct gcactcggtg cttctgggac tccagttcaa gttgaccatg    180
cacctgccgc acctccacgt attacggttc tgtttcggcg ccctcctcgt catgttgtcg    240
tgcatggcac accagtcgca ggagtggcag gacgtggtcc tgaccgactt accgttcctc    300
atgttcacgt tccagaggtt gtttcgggag gtcgggggt agctcttttg gtagaggttt    360
cggtttcccg tcggggctct tggtgtccac atgtgggacg ggggtagggc cctactcgac    420
tggttcttgg tccagtcgga ctggacggac cagtttccga agatagggtc gctgtagcgg    480
cacctcaccc tctcgttacc cgtcggcctc ttgttgatgt tctggtgcgg agggcacgac    540
ctgaggctgc cgaggaagaa ggagatgtcg ttcgagtggc acctgttctc gtccaccgtc    600
gtccccttgc agaagagtac gaggcactac gtactccgag acgtgttggt gatgtgcgtc    660
ttctcggaga gggacagagg cccatttcat ggctaggtct ttcaagtcct gctgtggttt    720
tggaattaat tttgctagca atgcgcatag ttgctgtagt cagtgtgggt cagccactcg    780
agatttgtct ttcaatgtcc ggacctgaag tagggcccag acgtgggcta ggactggaac    840
aggttttacc tggtctggga ccgacatatg gtcgtctaga attggaggta cggcagggca    900
ttgcaatagg tctagagatt gctggagctc ttggaagcgc tggacgacgt gcacgaccgt    960
aagaggttta ggacggtgga cggtacccga agtccagaac tctgagacct gagagacccg   1020
ccccaggacc ttcgtaggcc aatgtcgtgg cttcaacaac gagacagggc agacgtccca   1080
agggaagtcc tgtacgaaac cgtcgacctg acagaggcc  aacaattac ctagg          1135

<210> SEQ ID NO 15
<211> LENGTH: 374
<212> TYPE: PRT
<213> ORGANISM: Artificial
<220> FEATURE:
<223> OTHER INFORMATION: human metFc-OB protein analog 3

<400> SEQUENCE: 15

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30
```

```
Met Ile Ser Arg Thr Pro Glu Val Thr Cys Val Val Asp Val Ser
    35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
        115                 120                 125
Val Tyr Thr Leu Pro Pro Ser Arg Asp Glu Leu Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly Lys Val Pro Ile Gln Lys Val Gln Asp Asp Thr Lys Thr
225                 230                 235                 240
Leu Ile Lys Thr Ile Val Thr Arg Ile Asn Asp Ile Ser His Thr Gln
                245                 250                 255
Ser Val Ser Ser Lys Gln Lys Val Thr Gly Leu Asp Phe Ile Pro Gly
            260                 265                 270
Leu His Pro Ile Leu Thr Leu Ser Lys Met Asp Gln Thr Leu Ala Val
        275                 280                 285
Tyr Gln Gln Ile Leu Thr Ser Met Pro Ser Arg Asn Val Ile Gln Ile
    290                 295                 300
Ser Asn Asp Leu Glu Asn Leu Arg Asp Leu Leu His Val Leu Ala Phe
305                 310                 315                 320
Ser Lys Ser Cys His Leu Pro Trp Ala Ser Gly Leu Glu Thr Leu Asp
                325                 330                 335
Ser Leu Gly Gly Val Leu Glu Ala Ser Gly Tyr Ser Thr Glu Val Val
            340                 345                 350
Ala Leu Ser Arg Leu Gln Gly Ser Leu Gln Asp Met Leu Trp Gln Leu
        355                 360                 365
Asp Leu Ser Pro Gly Cys
    370

<210> SEQ ID NO 16
<211> LENGTH: 1135
<212> TYPE: DNA
<213> ORGANISM: Artificial
<220> FEATURE:
<223> OTHER INFORMATION: human metFc-OB protein analog 4; 5' to 3'

<400> SEQUENCE: 16
catatggaca aaactcacac atgcccaccg tgcccagctc cggaactcga aggtggtccg      60
tcagtcttcc tcttcccccc aaaacccaag gacaccctca tgatctcccg gacccctgag     120
```

```
gtcacatgcg tggtggtgga cgtgagccac gaagaccctg aggtcaagtt caactggtac    180
gtggacggcg tggaggtgca taatgccaag acaaagccgc gggaggagca gtacaacagc    240
acgtaccgtg tggtcagcgt cctcaccgtc ctgcaccagg actggctgaa tggcaaagct    300
tacgcatgcg cggtctccaa caaagccctc ccagccccca tcgagaaaac catctccaaa    360
gccaaagggc agccccgaga accacaggtg tacaccctgc ccccatcccg ggatgagctg    420
accaagaacc aggtcagcct gacctgcctg gtcaaaggct tctatcccag cgacatcgcc    480
gtggagtggg agagcaatgg gcagccggag aacaactaca agaccacgcc tcccgtgctg    540
gactccgacg gctccttctt cctctacagc aagctcaccg tggacaagag caggtggcag    600
caggggaacg tcttctcatg ctccgtgatg catgaggctc tgcacaacca ctacacgcag    660
aagagcctct ccctgtctcc gggtaaagta ccgatccaga agttcagga cgacaccaaa    720
accttaatta aaacgatcgt tacgcgtatc aacgacatca gtcacaccca gtcggtgagc    780
tctaaacaga aagttacagg cctggacttc atcccgggtc tgcacccgat cctgaccttg    840
tccaaaatgg accagaccct ggctgtatac cagcagatct aacctccat gccgtcccgt    900
aacgttatcc agatctctaa cgacctcgag aaccttcgcg acctgctgca cgtgctggca    960
ttctccaaat cctgccacct gccatgggct tcaggtcttg agactctgga ctctctgggc   1020
ggggtcctgg aagcatccgg ttacagcacc gaagttgttg ctctgtcccg tctgcagggt   1080
tcccttcagg acatgctttg gcagctggac ctgtctccgg gttgttaatg gatcc        1135

<210> SEQ ID NO 17
<211> LENGTH: 1135
<212> TYPE: DNA
<213> ORGANISM: Artificial
<220> FEATURE:
<223> OTHER INFORMATION: human metFc-OB protein analog 4; 3' to 5'

<400> SEQUENCE: 17
gtatacctgt tttgagtgtg tacgggtggc acgggtcgag gccttgagct tccaccaggc     60
agtcagaagg agaagggggg ttttgggttc ctgtgggagt actagagggc ctggggactc    120
cagtgtacgc accaccacct gcactcgtg cttctggaca tccagttcaa gttgaccatg    180
cacctgccgc acctccacgt attacggttc tgtttcggcg ccctcctcgt catgttgtcg    240
tgcatggcac accagtcgca ggagtggcag gacgtggtcc tgaccgactt accgtttcga    300
atgcgtacgc gccagaggtt gtttcggag gtcggggggt agctcttttg gtagaggttt     360
cggtttcccg tcggggctct tggtgtccac atgtgggacg ggggtagggc cctactcgac    420
tggttcttgg tccagtcgga ctggacggac cagtttccga agatagggtc gctgtagcgg    480
cacctcaccc tctcgttacc cgtcggcctc ttgttgatgt tctggtgcgg agggcacgac    540
ctgaggctgc cgaggaagaa ggagatgtcg ttcgagtggc acctgttctc gtccaccgtc    600
gtccccttgc agaagagtac gaggcactac gtactccgag acgtgttggt gatgtgcgtc    660
ttctcggaga gggacagagg cccatttcat ggctaggtct ttcaagtcct gctgtggttt    720
tggaattaat tttgctagca atgcgcatag ttgctgtagt cagtgtgggt cagccactcg    780
agatttgtct ttcaatgtcc ggacctgaag tagggcccag acgtgggcta ggactggaac    840
aggttttacc tggtctggga ccgacatatg gtcgtctaga attggaggta cggcagggca    900
ttgcaatagg tctagagatt gctggagctc ttggaagcgc tggacgacgt gcacgaccgt    960
aagaggttta ggacggtgga cggtaccgca agtccagaac tctgagacct gagagacccg   1020
ccccaggacc ttcgtaggcc aatgtcgtgg cttcaacaac gagacagggc agacgtccca   1080
```
agggaagtcc tgtacgaaac cgtcgacctg gacagaggcc caacaattac ctagg    1135

<210> SEQ ID NO 18
<211> LENGTH: 374
<212> TYPE: PRT
<213> ORGANISM: Artificial
<220> FEATURE:
<223> OTHER INFORMATION: human metFc-OB protein analog 4

<400> SEQUENCE: 18

Met Asp Lys Thr His Thr Cys Pro Pro Cys Pro Ala Pro Glu Leu Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Ala Tyr Ala Cys Ala Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Val Pro Ile Gln Lys Val Gln Asp Asp Thr Lys Thr
225                 230                 235                 240

Leu Ile Lys Thr Ile Val Thr Arg Ile Asn Asp Ile Ser His Thr Gln
                245                 250                 255

Ser Val Ser Ser Lys Gln Lys Val Thr Gly Leu Asp Phe Ile Pro Gly
            260                 265                 270

Leu His Pro Ile Leu Thr Leu Ser Lys Met Asp Gln Thr Leu Ala Val
        275                 280                 285

Tyr Gln Gln Ile Leu Thr Ser Met Pro Ser Arg Asn Val Ile Gln Ile
    290                 295                 300

Ser Asn Asp Leu Glu Asn Leu Arg Asp Leu Leu His Val Leu Ala Phe
305                 310                 315                 320

Ser Lys Ser Cys His Leu Pro Trp Ala Ser Gly Leu Glu Thr Leu Asp
                325                 330                 335

Ser Leu Gly Gly Val Leu Glu Ala Ser Gly Tyr Ser Thr Glu Val Val
            340                 345                 350

Ala Leu Ser Arg Leu Gln Gly Ser Leu Gln Asp Met Leu Trp Gln Leu
        355                 360                 365

```
Asp Leu Ser Pro Gly Cys
    370

<210> SEQ ID NO 19
<211> LENGTH: 4
<212> TYPE: PRT
<213> ORGANISM: Artificial
<220> FEATURE:
<223> OTHER INFORMATION: Linker 1

<400> SEQUENCE: 19

Ala Ala Ala Ala
1

<210> SEQ ID NO 20
<211> LENGTH: 5
<212> TYPE: PRT
<213> ORGANISM: Artificial
<220> FEATURE:
<223> OTHER INFORMATION: Linker 2

<400> SEQUENCE: 20

Ala Ala Ala Ala Ala
1               5

<210> SEQ ID NO 21
<211> LENGTH: 5
<212> TYPE: PRT
<213> ORGANISM: Artificial
<220> FEATURE:
<223> OTHER INFORMATION: Linker 3

<400> SEQUENCE: 21

Gly Gly Gly Gly Gly
1               5

<210> SEQ ID NO 22
<211> LENGTH: 7
<212> TYPE: PRT
<213> ORGANISM: Artificial
<220> FEATURE:
<223> OTHER INFORMATION: Linker 4

<400> SEQUENCE: 22

Gly Gly Gly Gly Gly Gly Gly
1               5

<210> SEQ ID NO 23
<211> LENGTH: 5
<212> TYPE: PRT
<213> ORGANISM: Artificial
<220> FEATURE:
<223> OTHER INFORMATION: Linker 5

<400> SEQUENCE: 23

Gly Gly Pro Gly Gly
1               5
```

We claim:
1. A protein having a formula selected from the group consisting of: $R_1$-$R_2$ and $R_1$-L-$R_2$, wherein:
$R_1$ is an Fc protein selected from the group consisting of:
(a) amino acids 1-233 of SEQ ID NO: 9, amino acids 1-233 of SEQ ID NO: 12, amino acids 1-228 of SEQ ID NO: 15, or amino acids 1-228 of SEQ ID NO: 18;
(b) the amino acid sequence of subpart (a) having a different amino acid substituted or deleted in one or more of the following positions (using the numbering according to SEQ. ID. NO. 9):
  (i) one or more cysteine residues replace by an alanine or serine residue;
  (ii) one or more tyrosine residues replaced by a phenylalanine residue;
  (iii) the amino acid at position 15 replaced with an glutamate;
  (iv) the amino acid at position 20 replaced with glutamate;
  (v) the amino acid at position 103 replaced with an alanine;
  (vi) the amino acid at position 105 replaced with an alanine;
  (vii) the amino acid at position 107 replaced with an alanine;
  (viii) the amino acids at positions 1, 2, 3, 4, and/or 5 deleted;
  (ix) the amino acid at position 15 replaced to ablate the Fc receptor binding site;
  (x) one or more amino acids at positions 98, 100, and 102 replaced to ablate the complement (C1q) binding site; and
  (xi) a combination of subparts i-x;
(c) the amino acid sequence of subparts (a) or (b) having a methionyl residue at the N-terminus;
(d) the amino acid sequence of subparts (a) through (c) wherein the Fc protein is connected to a water soluble polymer moiety selected from the group consisting of: polyethylene glycol, an ethylene glycol/propylene glycol copolymer, a carboxymethylcellulose, a dextran, a polyvinyl alcohol, a polyvinyl pyrolidone, a poly-1,3-dioxolane, a poly-1,3,6-trioxane, an ethylene/maleic anhydride copolymer, a polyaminoacid homopolymer, a polyaminoacid random copolymer, an albumin, a polylysine moiety, a poly(n-vinyl pyrolidone)polyethylene glycol, a propylene glycol homopolymer, a polypropylene oxide/ethylene oxide copolymer, a polyoxyethylated polyol, a polyethylene glycol propionaldehyde, a succinate, and a styrene;
(e) the amino acid sequence of subpart (d) wherein said water soluble polymer moiety is polyethylene glycol;
(f) the amino acid sequence of subpart (d) wherein said water soluble polymer is a polyamino acid-selected from the group consisting of an albumin, and a polylysine moiety; and
(g) the amino acid sequence of subpart (d) wherein said water soluble polymer moiety is attached at solely the N-terminus of said Fc protein;
$R_2$ is an OB protein selected from the group consisting of:
(A) the amino acid sequence 1-146 as set forth in SEQ. ID. NO. 3 or SEQ. ID. NO. 6;
(B) the amino acid sequence 1-146 as set forth in SEQ. ID. NO. 6 having a lysine residue at position 35 and an isoleucine residue at position 74;
(C) the amino acid sequence of subpart (B) wherein one or more of the following positions (using the numbering according to SEQ. ID. NO. 6): 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145; is substituted with the corresponding amino acid at the corresponding position as set forth in SEQ ID NO: 3;
(D) the amino acid sequence of subpart (B) wherein one or more of the following positions (using the numbering according to SEQ. ID. NO. 6) is substituted according to the following:
  (i) the amino acid at position 8 replaced with a serine;
  (ii) the amino acid at position 35 replaced with an arginine;
  (iii) the amino acid at position 48 replaced with a valine;
  (iv) the amino acid at position 53 replaced with a glutamine;
  (v) the amino acid at position 60 replaced with an isoleucine;
  (vi) the amino acid at position 66 replaced with an isoleucine;
  (vii) the amino acid at position 67 replaced with an asparagine;
  (viii) the amino acid at position 68 replaced with a leucine;
  (ix) the amino acid at position 89 replaced with a leucine;
  (x) the amino acid at position 100 replaced with a leucine;
  (xi) the amino acid at position 108 replaced with a glutamate;
  (xii) the amino acid at position 112 replaced with an aspartate; and
  (xiii) the amino acid at position 118 replaced with a leucine;
(E) the amino acid sequence of subparts (A), (B), (C), or (D) optionally lacking a glutaminyl residue at position 28;
(F) the amino acid sequence of subparts (A), (B), (C), (D), or (E) having a methionyl residue at the N-terminus,
(G) the OB protein of subpart (A) through (F) wherein the OB protein comprises a water soluble polymer moiety selected from the group consisting of: polyethylene glycol, an ethylene glycol/propylene glycol copolymer, a carboxymethylcellulose, a dextran, a polyvinyl alcohol, a polyvinyl pyrolidone, a poly-1,3-dioxolane, a poly-1,3,6-trioxane, an ethylene/maleic anhydride copolymer, a polyaminoacid homopolymer, a polyaminoacid random copolymer, an albumin, a polylysine moiety, a poly(n-vinyl pyrolidone)polyethylene glycol, a propylene glycol homopolymer, a polypropylene oxide/ethylene oxide copolymer, a polyoxyethylated polyol, a polyethylene glycol propionaldehyde, a succinate, and a styrene;
(H) the OB protein of subpart (G) wherein said water soluble polymer moiety is polyethylene glycol;
(I) the OB protein of subpart (G) wherein said water soluble polymer is a polyamino acid selected from the group consisting of an albumin, and a polylysine moiety; and
(J) the OB protein of subpart (G) wherein said water soluble polymer moiety is attached at solely the N-terminus of said OB protein; and
L is a linker.

2. The protein of claim 1 wherein the linker is one or more amino acids selected from the group consisting of: Glycine, Asparagine, Serine, Threonine and Alanine.

3. The protein of claim 1 wherein the linker is selected from the group consisting of:
(a) ala-ala-ala;
(b) ala-ala-ala-ala (SEQ ID NO:19);
(c) ala-ala-ala-ala-ala (SEQ ID NO:20);
(d) gly-gly;
(e) gly-gly-gly;
(f) gly-gly-gly-gly-gly (SEQ ID NO:21);
(g) gly-gly-gly-gly-gly-gly-gly (SEQ ID NO:22);
(h) gly-pro-gly;
(i) gly-gly-pro-gly-gly (SEQ ID NO:23);
(j) a chemical moiety; and
(k) any combination of subparts (a) through (j).

4. A pharmaceutical composition comprising an effective amount of the protein according to claim 1 in a pharmaceutically acceptable diluent, adjuvant or carrier.

* * * * *